US008226664B2

(12) United States Patent
Drews et al.

(10) Patent No.: US 8,226,664 B2
(45) Date of Patent: Jul. 24, 2012

(54) BIOLOGICAL UNIT REMOVAL TOOLS WITH MOVABLE RETENTION MEMBER

(75) Inventors: Michael J. Drews, Palo Alto, CA (US); Dennis Westerling, Sunnyvale, CA (US); Timothy J. Kirkley, Sunnyvale, CA (US)

(73) Assignee: Restoration Robotics, Inc., Mountain View, CA (US)

( * ) Notice: Subject to any disclaimer, the term of this patent is extended or adjusted under 35 U.S.C. 154(b) by 208 days.

(21) Appl. No.: 12/403,605

(22) Filed: Mar. 13, 2009

(65) Prior Publication Data
US 2009/0240261 A1    Sep. 24, 2009

Related U.S. Application Data

(60) Provisional application No. 61/037,701, filed on Mar. 18, 2008, provisional application No. 61/147,090, filed on Jan. 24, 2009.

(51) Int. Cl.
*A61B 17/50* (2006.01)

(52) U.S. Cl. ...................................................... 606/133

(58) Field of Classification Search .................. 600/562, 600/564–568; 606/131, 133, 184, 185, 187
See application file for complete search history.

(56) References Cited

U.S. PATENT DOCUMENTS

| 3,561,429 A | 2/1971 | Jewett |
| 3,605,721 A | 9/1971 | Hallac |
| 3,998,230 A | 12/1976 | Miller |
| 4,160,453 A | 7/1979 | Miller |
| 4,393,872 A | 7/1983 | Reznik et al. |
| 4,427,014 A | 1/1984 | Bel et al. |
| 4,479,291 A | 10/1984 | Yamada |
| 4,640,296 A | 2/1987 | Snepp-Pesch et al. |
| 4,716,901 A | 1/1988 | Jackson et al. |
| 4,785,826 A | 11/1988 | Ward |
| 5,036,860 A | 8/1991 | Leigh et al. |
| 5,183,053 A | 2/1993 | Yeh et al. |
| 5,341,816 A | 8/1994 | Allen |
| 5,423,330 A | 6/1995 | Lee |
| 5,439,475 A | 8/1995 | Bennett |

(Continued)

FOREIGN PATENT DOCUMENTS
EP    0966920    12/1999
(Continued)

OTHER PUBLICATIONS

PCT Notification Concerning Transmittal of International Preliminary Report on Patentability. International Application No. PCT/US2008/003623. Form PCT/IB/326 & 373, and PCT/ISA/237. Mailed Oct. 1, 2009. (10 Pages).

(Continued)

*Primary Examiner* — Ryan Severson
(74) *Attorney, Agent, or Firm* — Lena I. Vinitskaya; Sharon Upham

(57) ABSTRACT

Tools and methods of use for removing biological units from a body surface utilizing a removal tool are disclosed. The tool incorporates a retention member configured to impede movement of the biological unit in the direction of a distal end of the tool and to improve retention of the biological unit in the tool. The retention member is radially movable within the lumen of the biological unit removal tool. The distal tips of the tools are desirably configured to reduce the chance of transection of a biological unit.

28 Claims, 17 Drawing Sheets

SECTION F-F

U.S. PATENT DOCUMENTS

| | | | |
|---|---|---|---|
| 5,480,388 | A | 1/1996 | Zadini et al. |
| 5,562,613 | A | 10/1996 | Kaldany |
| 5,573,008 | A * | 11/1996 | Robinson et al. ............. 600/567 |
| 5,584,841 | A | 12/1996 | Rassman |
| 5,693,064 | A | 12/1997 | Arnold |
| 5,782,851 | A | 7/1998 | Rassman |
| 5,782,853 | A | 7/1998 | Zeevi et al. |
| 5,788,651 | A | 8/1998 | Weilandt |
| 5,792,163 | A | 8/1998 | Hitzig |
| 5,794,626 | A | 8/1998 | Kieturakis |
| 5,817,120 | A | 10/1998 | Rassman |
| 5,827,199 | A | 10/1998 | Alexander |
| 5,827,297 | A | 10/1998 | Boudjema |
| 5,885,226 | A | 3/1999 | Rubinstein et al. |
| 5,893,853 | A | 4/1999 | Arnold |
| 5,895,403 | A | 4/1999 | Collinsworth |
| 5,910,121 | A | 6/1999 | Paolo et al. |
| 5,961,529 | A | 10/1999 | Arnold |
| 6,015,391 | A | 1/2000 | Rishton et al. |
| 6,059,807 | A | 5/2000 | Boudjema |
| 6,080,175 | A | 6/2000 | Hogendijk |
| 6,086,543 | A | 7/2000 | Anderson et al. |
| 6,110,127 | A | 8/2000 | Suzuki |
| 6,110,189 | A | 8/2000 | Markman |
| 6,120,521 | A | 9/2000 | Casparian |
| 6,142,955 | A | 11/2000 | Farascioni et al. |
| 6,273,861 | B1 | 8/2001 | Bates et al. |
| 6,315,737 | B1 | 11/2001 | Skinner |
| 6,395,002 | B1 | 5/2002 | Ellman et al. |
| 6,416,484 | B1 | 7/2002 | Miller et al. |
| 6,461,369 | B1 | 10/2002 | Kim |
| 6,471,709 | B1 | 10/2002 | Fawzi et al. |
| 6,488,636 | B2 | 12/2002 | Bryan et al. |
| 6,554,779 | B2 | 4/2003 | Viola et al. |
| 6,572,625 | B1 | 6/2003 | Rassman |
| 6,585,746 | B2 | 7/2003 | Gildenberg |
| 6,875,220 | B2 | 4/2005 | Du et al. |
| 6,918,880 | B2 | 7/2005 | Brookner et al. |
| 6,939,318 | B2 | 9/2005 | Stenzel |
| 7,014,614 | B2 | 3/2006 | Casula |
| 7,172,604 | B2 | 2/2007 | Cole |
| 7,201,722 | B2 | 4/2007 | Krueger |
| 7,261,721 | B2 | 8/2007 | Feller |
| 7,762,959 | B2 | 7/2010 | Bilsbury |
| 7,775,989 | B2 | 8/2010 | Nakao |
| 2001/0034534 | A1 | 10/2001 | Transue |
| 2002/0103500 | A1 | 8/2002 | Gildenberg |
| 2002/0151821 | A1 | 10/2002 | Castellacci |
| 2003/0097079 | A1 | 5/2003 | Garcia |
| 2003/0097144 | A1 | 5/2003 | Lee |
| 2004/0092924 | A1 | 5/2004 | Vasa |
| 2004/0116942 | A1 | 6/2004 | Feller |
| 2004/0220589 | A1* | 11/2004 | Feller ............................ 606/133 |
| 2005/0043718 | A1 | 2/2005 | Madhani et al. |
| 2005/0085838 | A1 | 4/2005 | Thompson et al. |
| 2005/0090809 | A1 | 4/2005 | Cooper et al. |
| 2005/0096687 | A1 | 5/2005 | Rassman et al. |
| 2005/0131313 | A1 | 6/2005 | Mikulka et al. |
| 2005/0187573 | A1 | 8/2005 | Rassman et al. |
| 2005/0245952 | A1 | 11/2005 | Feller |
| 2005/0267506 | A1 | 12/2005 | Harris |
| 2006/0161179 | A1 | 7/2006 | Kachenmeister |
| 2006/0173476 | A1 | 8/2006 | Bradica et al. |
| 2006/0178678 | A1 | 8/2006 | Cole |
| 2007/0078466 | A1 | 4/2007 | Bodduluri et al. |
| 2007/0078473 | A1 | 4/2007 | Bodduluri et al. |
| 2007/0106307 | A1 | 5/2007 | Bodduluri et al. |
| 2007/0123800 | A1 | 5/2007 | Nishtala et al. |
| 2007/0142743 | A1 | 6/2007 | Provencher et al. |
| 2007/0149985 | A1 | 6/2007 | Cole |
| 2007/0156164 | A1 | 7/2007 | Cole |
| 2007/0213634 | A1 | 9/2007 | Teague |
| 2007/0213741 | A1 | 9/2007 | Cole |
| 2008/0033455 | A1 | 2/2008 | Rassman et al. |
| 2008/0045858 | A1 | 2/2008 | Tessitore et al. |
| 2008/0154150 | A1 | 6/2008 | Goldenberg |
| 2008/0154296 | A1 | 6/2008 | Taylor et al. |
| 2008/0234602 | A1 | 9/2008 | Oostman et al. |
| 2008/0234698 | A1 | 9/2008 | Oostman et al. |
| 2008/0234699 | A1 | 9/2008 | Oostman et al. |
| 2009/0227895 | A1 | 9/2009 | Goldenberg |
| 2010/0082042 | A1 | 4/2010 | Drews et al. |
| 2011/0245845 | A1 | 10/2011 | Oostman, Jr. |

FOREIGN PATENT DOCUMENTS

| | | |
|---|---|---|
| EP | 1293167 | 3/2003 |
| GB | 2006017 | 5/1979 |
| SE | 539 729 C2 | 8/2008 |
| WO | 97/06749 | 2/1997 |
| WO | 02/07602 | 1/2002 |
| WO | 02/065919 | 8/2002 |
| WO | 2005/109799 | 11/2005 |
| WO | 2006/081556 | 8/2006 |
| WO | 2007021904 | 2/2007 |
| WO | 2008027829 | 3/2008 |
| WO | 2009/017445 | 2/2009 |

OTHER PUBLICATIONS

Inaba, M. and Inaba, Y., "Androgenetic Alopecia, Modern Concepts of Pathogenesis and Treatment", 29. Operative Treatment for Androgenetic Alopecia, Springer, 1996, pp. 238-244, 309. (9 pages).

Harris, James, A., "New Methodology and Instrumentation for Follicular Unit Extraction: Lower Follicle Transection Rates and Expanded Patient Candidacy," Department of Otolaryngology/Head and Neck Surgery, Univ. of Colorado Health Sciences Center, Denver, Colorado; Copyright 2006 by the American Society of Dermatologic Surgery, Inc. Published by BC Decker, Inc., Dermatologic Surgery, vol. 32, Jan. 1, 2006 (7 pages).

PCT Int'l Search Report and Written Opinion in PCT/US2008/003623, Applicant Restoration Robotics, Inc., Forms PCT/ISA/210 and 237, dated Nov. 12, 2008 (14 pages).

PCT Int'l Search Report and Written Opinion in PCT/US2009/037132, Forms PCT/ISA/220, PCT/ISA/210 and PCT/ISA/237. Applicant Restoration Robotics, Inc., dated May 27, 2009 (17 pages).

Robert M. Bernstein, MD; William R. Rassman, MD. "New Instrumentation for Three-Step Follicular Unit Extraction". Hair Transplant Forum International, vol. 16, No. 1, Jan./Feb. 2006.

Non-Final Office Action mailed Oct. 27, 2010, in relation to commonly assigned U.S. Appl. No. 12/050,913 (21 pages).

PCT Int'l Search Report and Written Opinion in connection with commonly assigned PCT/US2009/056775, Applicant: Restoration Robotics, Inc. Forms PCT/ISA/220, 210 and 237, dated Jan. 12, 2010, (14 pages).

Office Action mailed Apr. 27, 2011, in relation to commonly assigned U.S. Appl. No. 12/050,907 (20 pages).

Final Office Action mailed Apr. 26, 2011, in relation to commonly assigned U.S. Appl. No. 12/050,913 (24 pages).

Office Action mailed Mar. 28, 2011, in relation to commonly assigned U.S. Appl. No. 12/050,917 (19 pages).

PCT Notification concerning Transmittal of International Preliminary Report on Patentabiltity in connection with commonly assigned International Application PCT/US2009/056775, Applicant Restoration Robotics, Inc., Forms PCT/IB/326, PCT/IB/373, and PCT/ISA/237, dated Apr. 14, 2011. (8 pages).

Response filed Jul. 26, 2011 to Final Office Action dated Apr. 26, 2011, in relation to commonly assigned U.S. Appl. No. 12/050,913 (12 pages).

Response filed Jul. 27, 2011 to Office Action dated Mar. 28, 2011, in relation to commonly assigned U.S. Appl. No. 12/050,917 (10 pages).

Non-Final Office Action dated Mar. 6, 2012, in relation to commonly assigned U.S. Appl. No. 12/752,889 (12 pages).

Non-Final Office Action dated Oct. 25, 2011, in relation to commonly assigned U.S. Appl. No. 12/050,917 (13 pages).

* cited by examiner

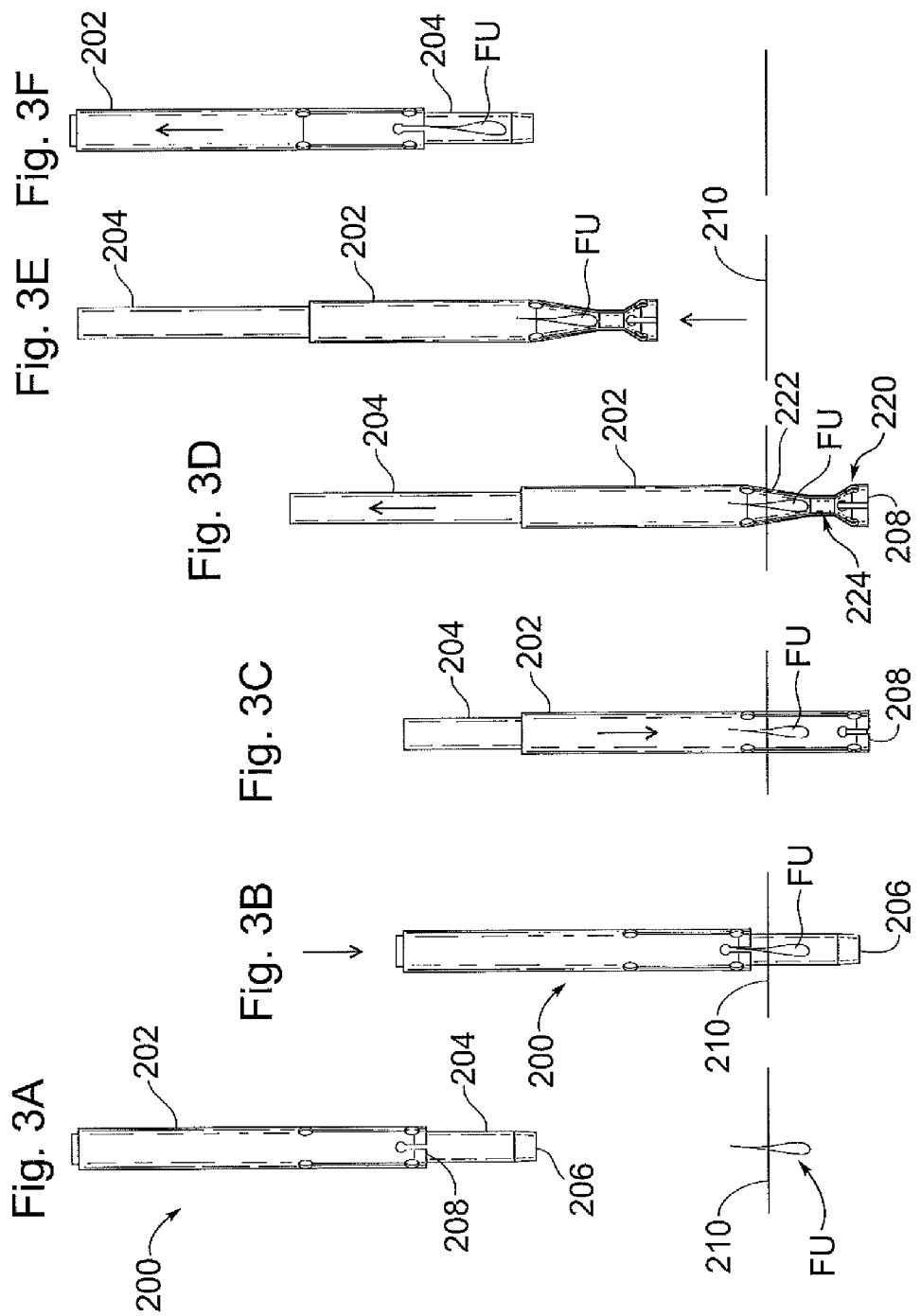

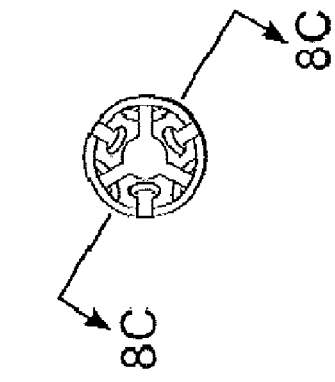
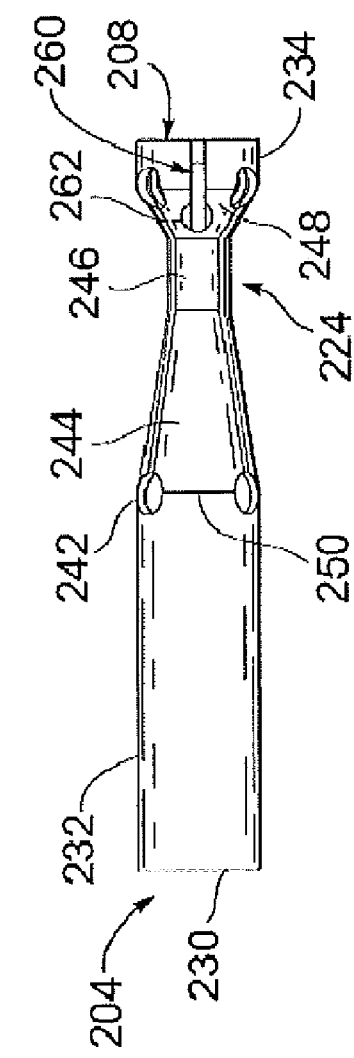
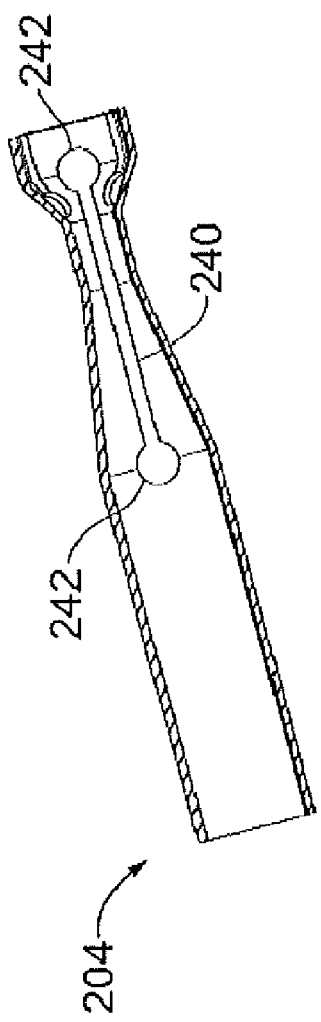

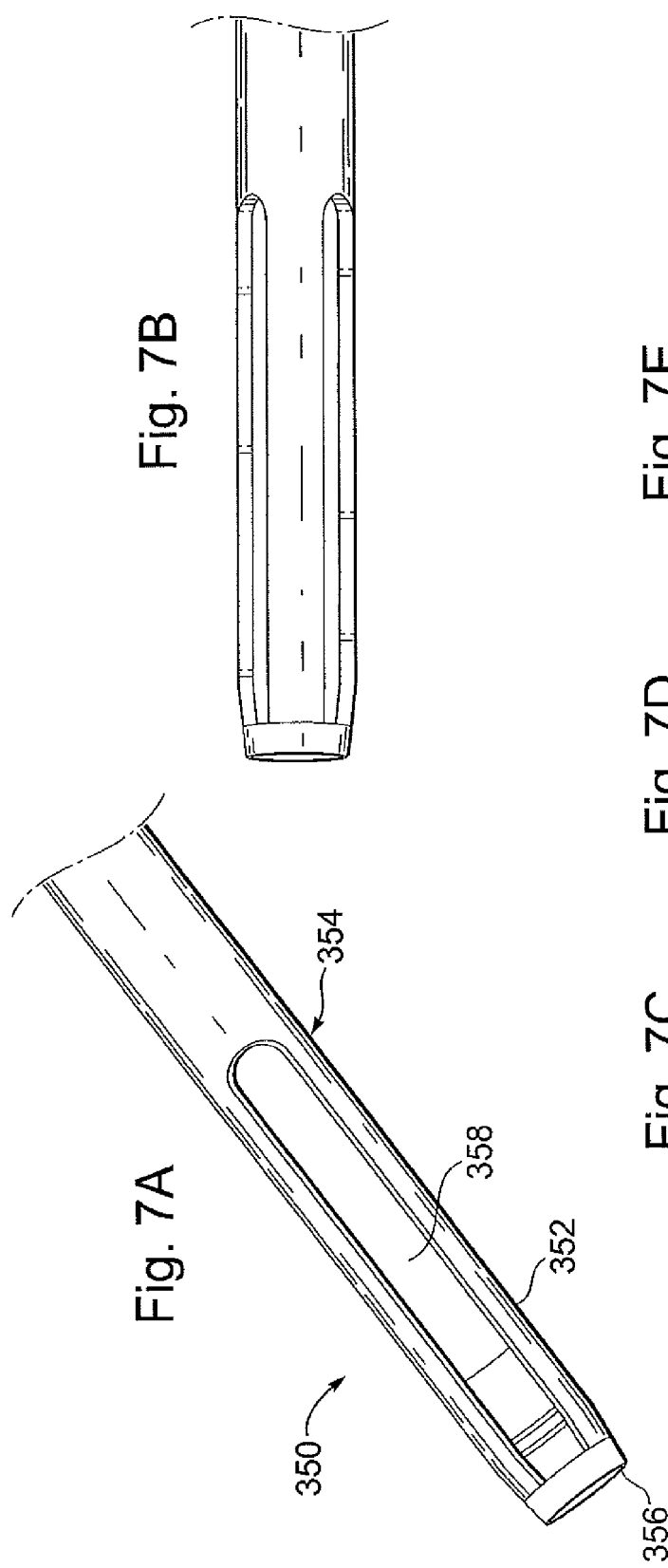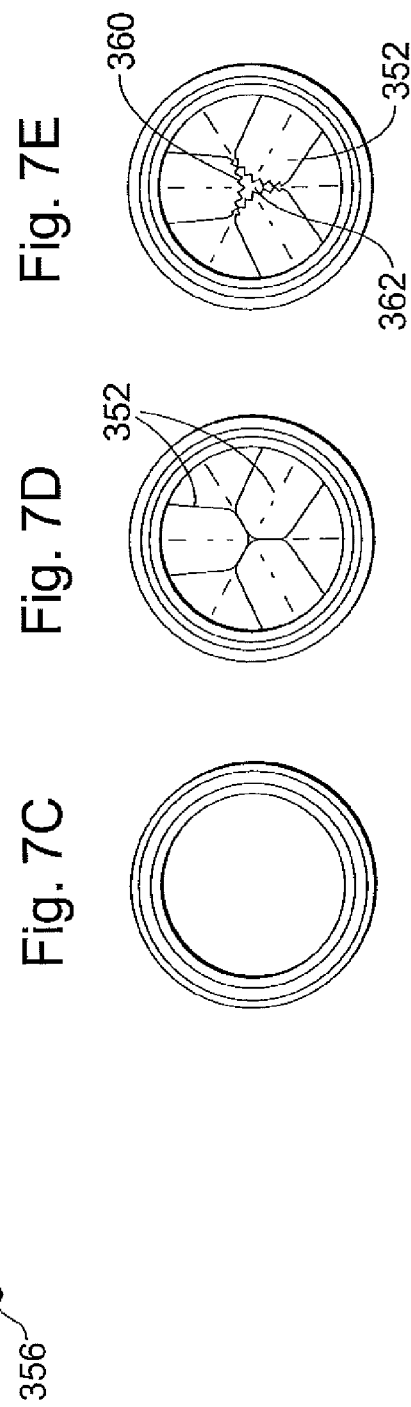

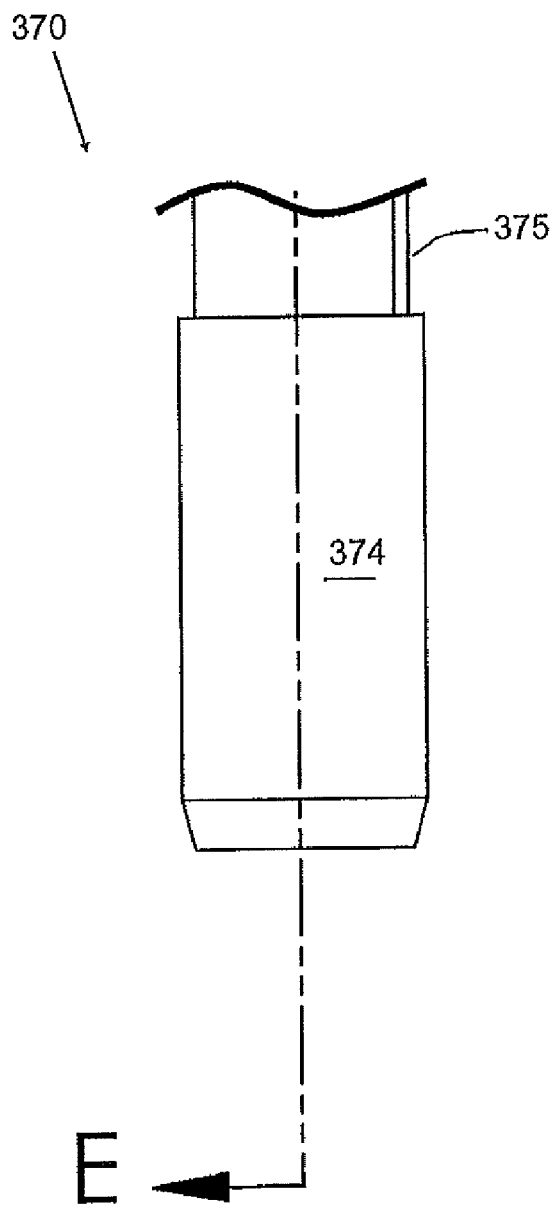
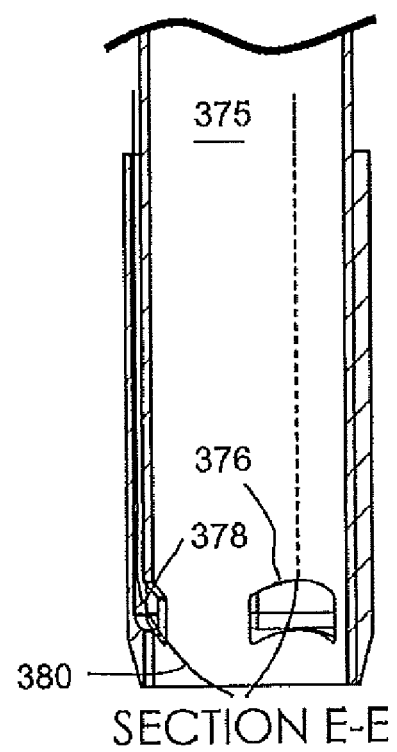
Fig. 9A
Fig. 9B

SECTION G-G

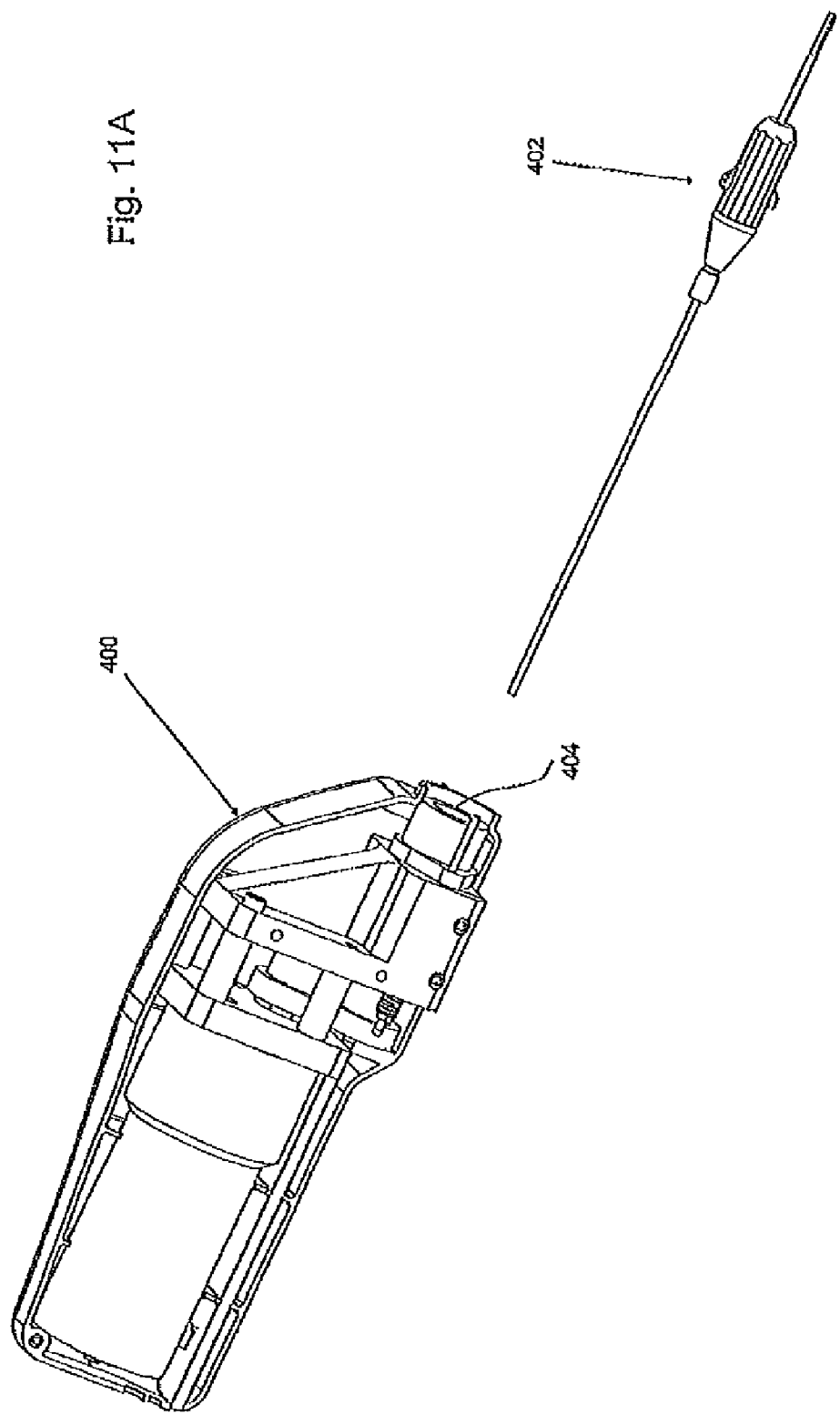

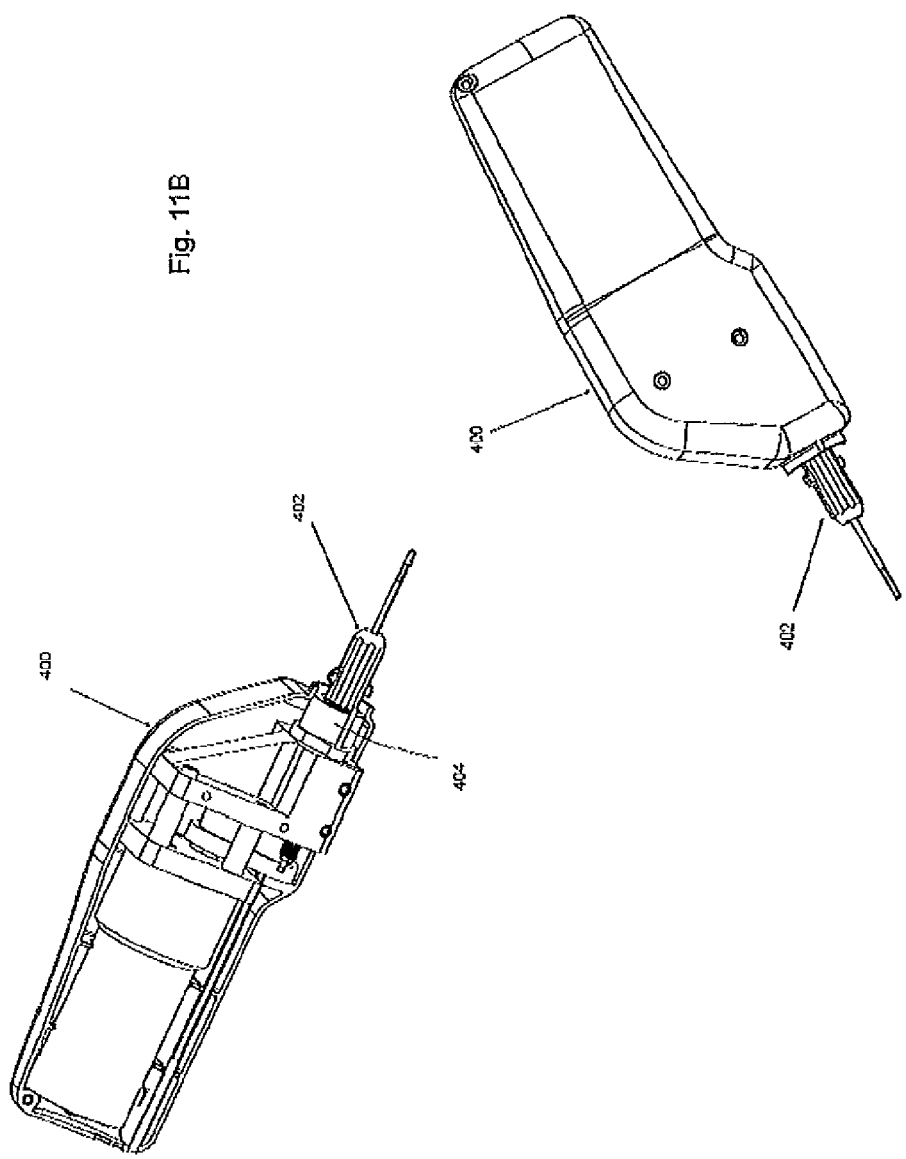

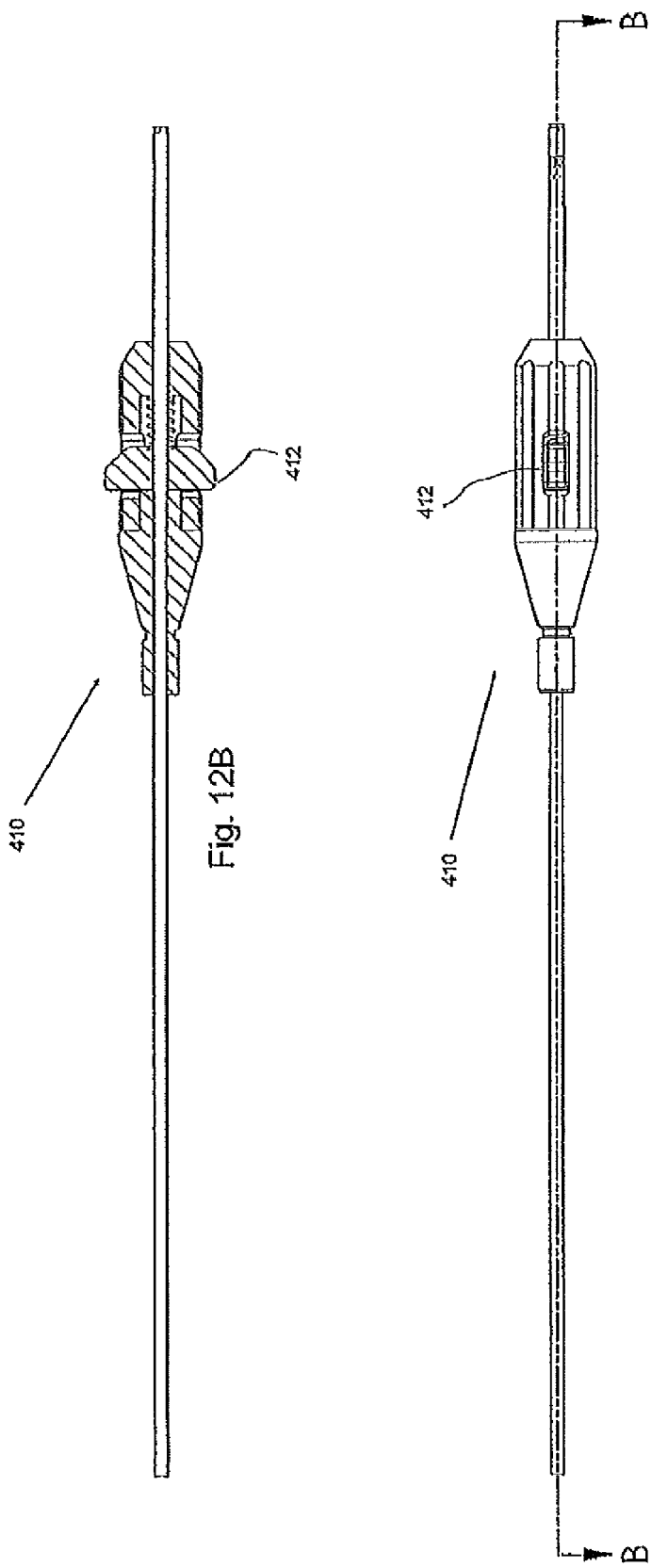

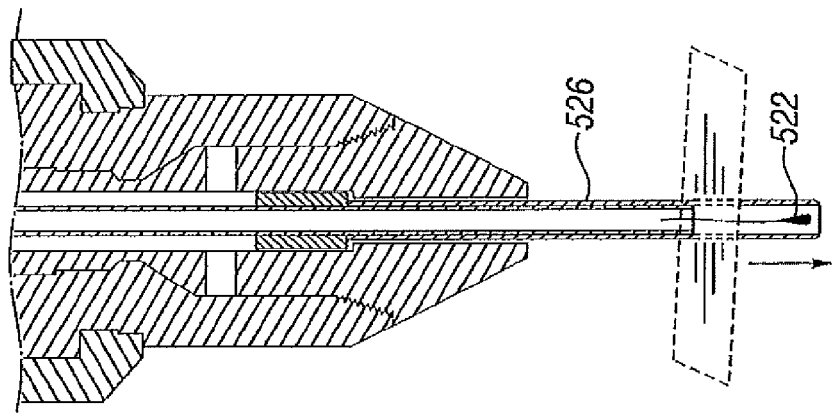
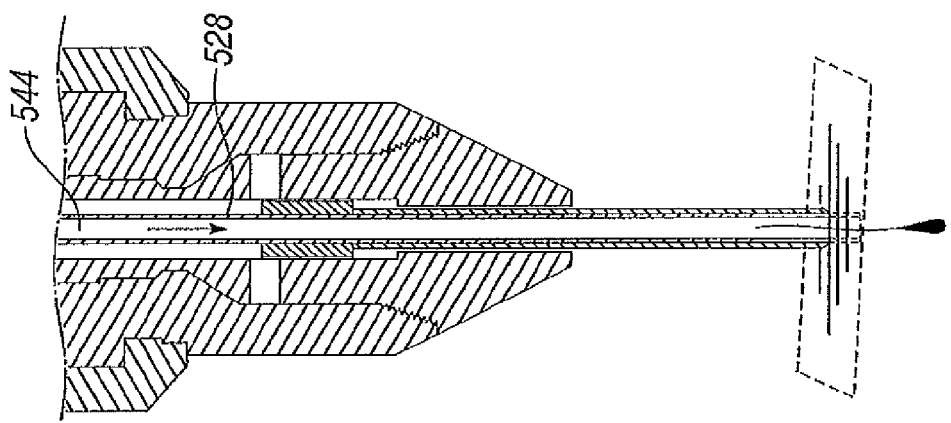
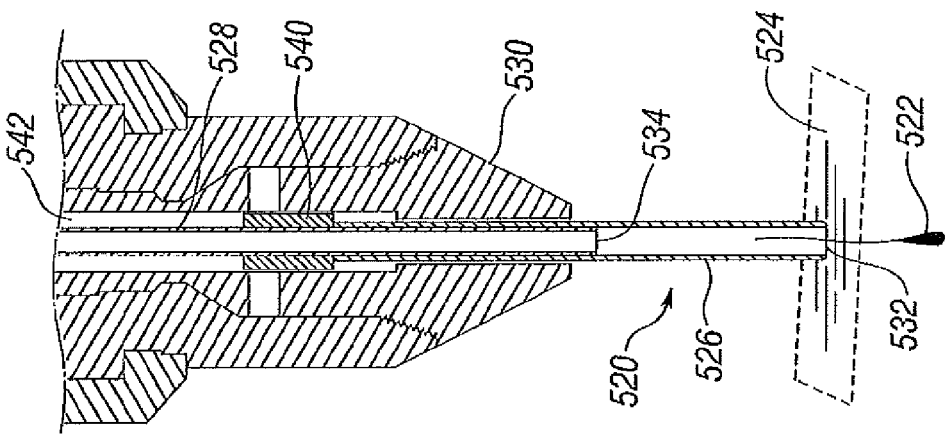

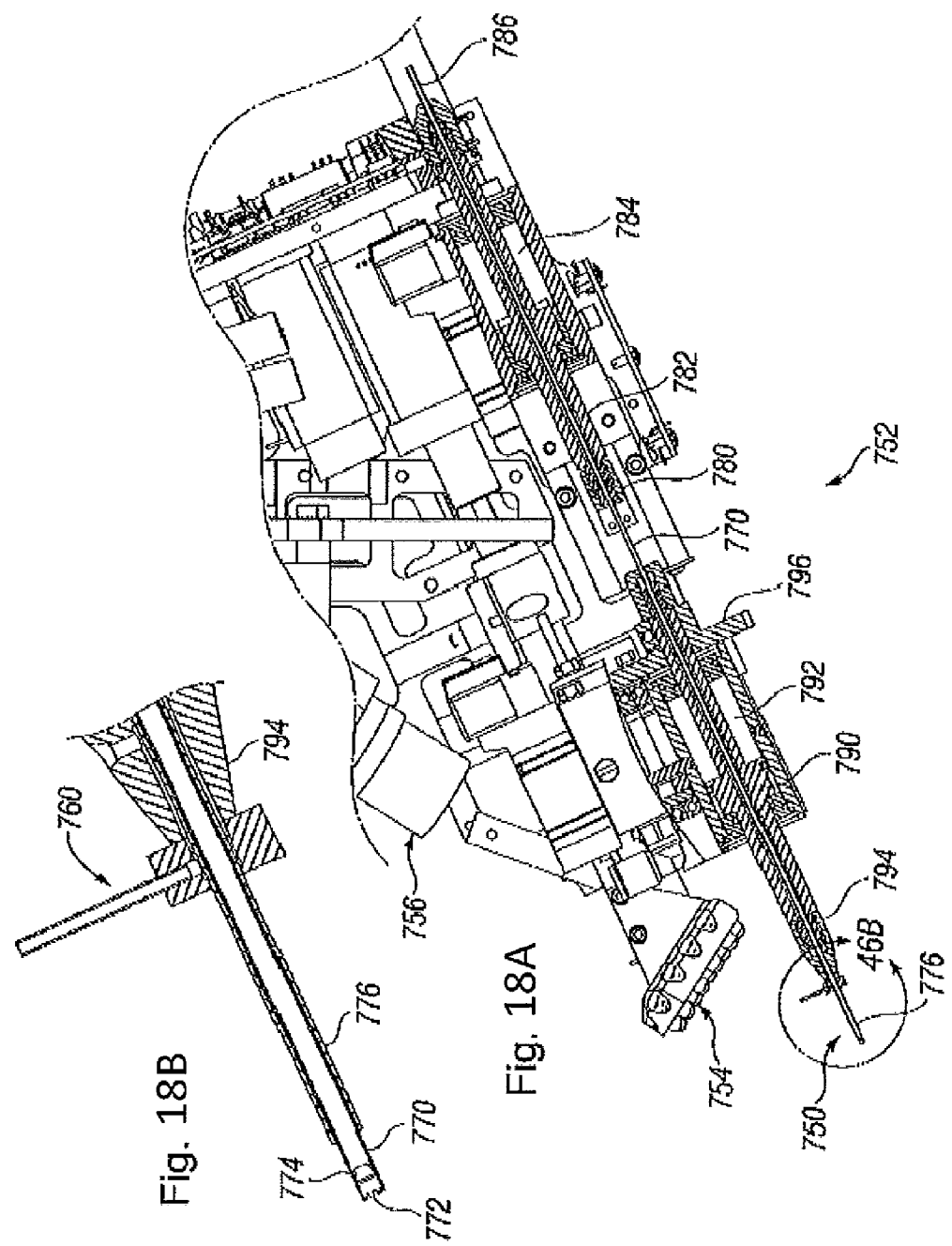

BIOLOGICAL UNIT REMOVAL TOOLS WITH MOVABLE RETENTION MEMBER

RELATED APPLICATIONS

This application claims priority under 35 U.S.C. 119(e) to U.S. Provisional Application No. 61/037,701 filed Mar. 18, 2008, entitled BIOLOGICAL UNIT REMOVAL TOOL WITH CONSTRICTOR, and to U.S. Provisional Application No. 61/147,090, filed Jan. 24, 2009, entitled BIOLOGICAL UNIT REMOVAL TOOLS WITH MOVABLE RETENTION MEMBERS.

FIELD OF THE INVENTION

This invention relates generally to tools used for the harvesting of various biological tissue samples, including hair follicles.

BACKGROUND OF THE INVENTION

There are various known tools and instruments for removing biological tissue samples from the body. For example, biopsy needles and punches are used when a small tissue specimen is required for examination, for example, to identify certain medical conditions. Another example of the biological tissue which is often desired to be removed or harvested is a hair follicle. Hair transplantation procedures are well-known, and typically involve harvesting donor hair grafts from the "donor areas," for example, side and back fringe areas of the patient's scalp, and implanting them in a bald area ("recipient area"). Historically, the harvested hair grafts were relatively large (3-5 mm), although more recently the donor grafts may be single "follicular units," which are naturally occurring aggregates of 1-3 (and much less commonly, 4-5) closely spaced hair follicles that are distributed randomly over the surface of the scalp. In one well-known process, a linear portion of the scalp is removed from a donor area by dissection, using a scalpel to cut down into the fatty subcutaneous tissue. The strip is then dissected (under a microscope) into the component follicular units, which are then implanted into a recipient area in respective puncture incisions made by a needle or razor blade. Forceps are typically used to grasp and place the follicular unit grafts into the needle puncture locations, although other instruments and methods are known for doing so.

In "Androgenetic Alopecia" (Springer 1996), M. Inaba & Y. Inaba disclose and describe a method for harvesting singular follicular units utilizing a hollow needle punch having a cutting edge and an interior lumen with a diameter of 1 mm, which is about equal to the diameter of critical anatomical parts of a follicular unit. The needle punch is axially aligned with an axis of a follicular unit to be extracted and then advanced into the scalp to cut the scalp about the circumference of the selected follicular unit. Thereafter, the follicular units are easily removed, e.g., using forceps, for subsequent implantation into a recipient site with a specially devised insertion needle.

U.S. Pat. No. 7,172,604 (Cole) discloses an instrument for the extraction of individual follicular units. Several steps in a process disclosed in Cole for extracting a hair follicle from the skin are shown in FIGS. 1A-1C. FIG. 1 shows a section of skin 20 containing a hair follicle 22 with a hair 24 disposed therein, wherein a tubular harvesting punch 26 contacts the surface of the skin. The punch 26 contacts the skin at an angle with respect to the skin's surface over the location at which the hair 24 emerges from the skin. A sharp end of the punch 26 penetrates the skin and advances to a depth D of between about 0.05-0.5 millimeters. The surgeon then angles the punch 26 to an angle along the same axis as the hair growth, and further advances the punch into the dermis to a second depth $D_2$ of 2-7 millimeters.

Published U.S. Patent Application 20050267506 (Harris) discloses a method and apparatus for the extraction of follicular units by first scoring the outer skin layers with a sharp punch, removing the sharp punch, and then inserting a blunt punch into the incision to separate the hair follicular unit from the surrounding tissue and fatty layer to reduce the incidence of hair transection. Another U.S. Pat. No. 6,585,746 (Gildenberg) discloses a hair transplantation system utilizing a robotic system, including a robotic arm and a hair follicle end effector associated with the robotic arm that could be used to harvest hair follicles from the donor area.

SUMMARY OF THE INVENTION

The present invention provides a number of solutions to deficiencies in the prior art and includes various features for increasing the yield of usable harvested biological specimens for instance a follicular unit, a skin sample, a tissue sample, or a biopsy unit. In general the invention provides tools that effectively penetrate tissue and remove and retain biological units therein without damaging them. One particularly useful application for the tools described herein is in the area of hair harvesting and transplantation, which requires the removal of countless follicular units. The tools can be manually operated or incorporated into an automated system, including robotic system.

One aspect of the invention is a biological tissue removal tool comprising an inner elongated body which has a lumen sized to receive a biological unit and a distal tip configured to penetrate a body surface, and an outer elongated body axially movable over the inner elongated body and having a retention member. The retention member moves between a retracted position and a retention position depending upon the relative axial positions of the respective elongated bodies.

Another aspect of the invention is a biological tissue removal tool comprising an elongated body and at least one movable retention member. The elongated body has a lumen sized to receive a biological unit and a distal end with a distal tip configured to penetrate a body surface. At least a portion of the retention member is axially movable over the elongated body and the retention member is radially movable between a retracted position and a retention position, such that in the retention position at least a distal tip of the retention member extends beyond the distal tip of the elongated body and converges.

In yet another aspect of the invention is a biological tissue removal tool comprising an elongated body which has a lumen sized to receive a biological unit, a distal end with a distal tip configured to penetrate tissue. A retention member is axially movable with respect to the elongated body and radially movable from a retracted position to a retention position. In the retraction position the retention member is substantially disposed within the elongated body, and in the retention position at least a portion of the retention member extends beyond the distal tip of the elongated body. The elongated body further comprises a structure configured to guide at least a portion of a retention member to converge.

In yet still another aspect of the invention, methods of operation corresponding to certain aspects of the various above removal tools are provided. In some embodiments, the biological unit is a follicular unit and the removal tools are hair harvesting tools. In further embodiments, the tool is configured for use in a robotic hair harvesting system.

It should be understood that the various retention features of the removal tools of the invention can be used in combination with other features of the inventions described herein. For example, any of the retention features of the removal tool of the present invention can be incorporated into a single tube or cannula, or it could form a part of an inner or outer cannula of a concentric tubes removal tool. The tools of the invention may be used for removal of biological units, including hair harvesting and/or transplantation. Likewise, various combinations of features can be incorporated into a manual, semi-automatic, or fully automated system, including a robotic system. In short, unless stated otherwise, any combination of features described herein are contemplated.

Other and further objects and advantages of the invention will become apparent from the following detailed description when read in view of the accompanying figures.

BRIEF DESCRIPTION OF THE DRAWINGS

Features and advantages of the present invention will become appreciated as the same become better understood with reference to the specification, claims, and appended drawings wherein:

FIG. 2A shows the outline of a biological unit removed from a body surface by a harvesting tool advanced at an angle to the surface, while

FIGS. 3A-3F illustrate a sequence of steps of operation of an exemplary biological unit removal tool of the present invention in the process of removing a follicular unit from the body surface;

FIGS. 4A-4C are elevational and sectional views of an exemplary outer tube having a constrictive retention member of the biological unit removal tool of the FIG. 3A-3F;

FIGS. 7A-7E are various alternative views of the biological unit removal tool similar to one in FIGS. 5A and 5B;

FIGS. 9A-9B are side and longitudinal sectional views, respectively, of a another exemplary embodiment of the biological unit removal tool of the invention having movable tines and a protective outer sheath;

FIGS. 11A-11C are exploded and assembled perspective views of a semi-automated handpiece or tool for controlling the various biological unit removal tools of the invention;

FIGS. 12A-12B are side and longitudinal sectional views, respectively, of an exemplary biological unit removal tool in accordance with the invention that can be incorporated into a more automated system;

FIGS. 13A-13C are longitudinal sectional views of three stages of operation of an embodiment according to another aspect of the present invention directed to a concentric tube concept for the biological unit removal tools;

FIGS. 18A and 18B are perspective views of yet another embodiment of the biological unit removal tool incorporated in the exemplary robotically-operated system for hair removal and implantation.

DETAILED DESCRIPTION OF THE PREFERRED EMBODIMENTS

Figure 1A:
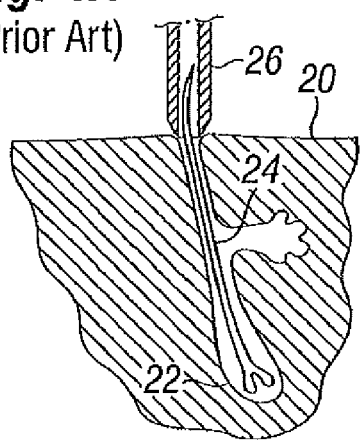
FIGS. 1A-1C show a section of skin containing a hair follicle in contact with a portion of a tool of the prior alt.
Figure 1B:
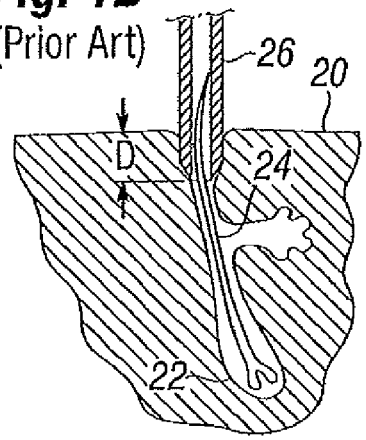
Figure 1C:
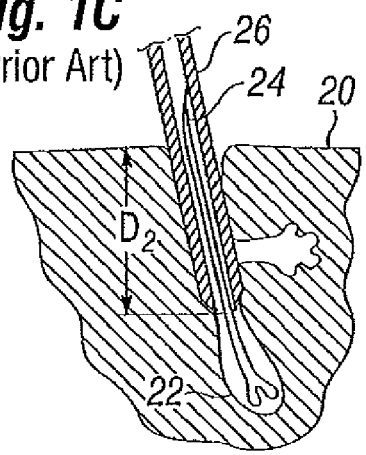
Figure 2A:
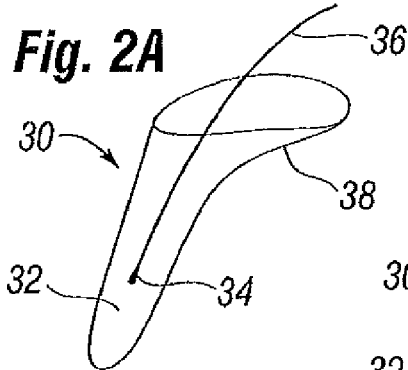
Figure 2B:
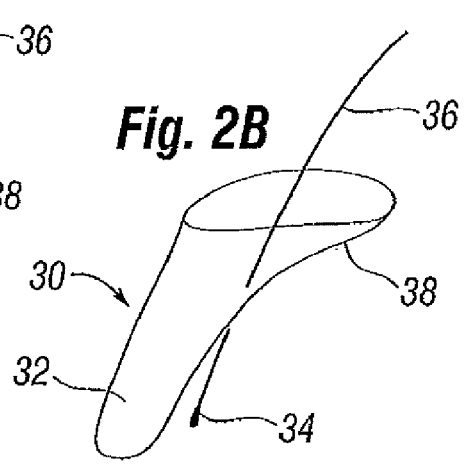
FIG. 2B shows the same biological unit and the resulting hair transection.

Sometimes, the sharp end of the needle punch cuts through, or transects, the hair shaft, rendering the follicular unit less than desirable. At other times, the incident angle at which the hollow punch contacts the skin surface causes the punch to stretch the skin and cut a relatively large flap of surrounding tissue along with the hair follicle, which may interfere with a subsequent implant procedure. To illustrate certain problems associated with the existing devices for removal of the biological tissue specimens, including specifically follicular unit harvesting, FIG. 2A shows the outline of a typical biological unit 30 removed from a body surface by a tubular harvesting cannula (not shown) advanced at an angle to the surface. The cannula generally removes a tissue plug 32, preferably centered in the example shown around a follicular unit having a bulb 34 and shaft 36. However, because the cannula advances into the skin at an angle, an undesirable lateral flap 38 of skin in the direction that the cannula is angled may result. This appendage or flap 38 occurs more often in high-speed punching using a harvesting cannula or needle and low angles of incidence from the body surface, such as between 15-45°. The flap 38 may interfere with movement of the biological unit 30 through the harvesting tool, its removal from the body surface and its retention in the removal tool. Moreover, in case of subsequent implantation of the harvested hair, the existence of the flap 38 interferes with the preference for small and closely spaced incisions at the implantation site. FIG. 2B shows an additional problem associated with the sliding of the cannula before a complete penetration of the skin while being advanced at an angle which results again in the creation of the flap and also in biological unit 30 being transected along the shaft 36. These two problems are typical reasons for discarding harvested biological units 30 used in hair transplantation, and may also be undesirable for biopsy or other applications where specimens of biological tissue need to be taken.

Despite certain advances in improving the tools for harvesting of biological tissue, there remains a need for a more efficient harvesting tool that increases the yield of usable harvested specimens, improves retention of the harvested units in the removal tool and the quality of the obtained specimens.

In the following Detailed Description, reference is made to the accompanying drawings that show by way of illustration some exemplary embodiments in which the invention may be practiced. In this regard, directional terminology, such as "top," "bottom," "front," "back," "distal," "proximal," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated systems described herein may also be robotically-assisted or computer/software/machine-instruction controlled. The devices and methods of the present invention are useful in manual procedures and systems, as well as in automated procedures and system. The tools of the present invention could be used with the robotically-assisted systems and procedures. The adverb "automatically" when referring to use of a particular component of a system or a particular step in a process means that such step is accomplished autonomously, i.e., without real-time manual assistance.

The term "tool" or "biological unit removal tool" as used herein refers to any number of tools or end effectors that are capable of removing or harvesting various biological tissues, for example, follicular units ("FUs") from a body surface. In general, however, the tools of the present invention may be useful for removing biological units other than FUs from a body surface. In this sense, a body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The distal end of removal tools (for example, punches, coring devices, cutting and/or trimming devices, needles), are typically sharpened, to cut and extract the tissue (e.g., hair follicle). The terms "coupled," or "attached," or "connected," or "mounted" as used herein, may mean directly or indirectly coupled, attached, integrated, or mounted through one or more intervening components.

Various embodiments of follicular unit harvesting cannulas (or tools) described herein may be employed in harvesting systems, whether such systems are fully-automated (e.g., robotically controlled), semi-automated, or manually controlled. It will be appreciated by those skilled in the art that each harvesting cannula design may have certain benefits (e.g., superior retraction and retention of follicular units, less trauma to the surrounding skin and tissue), or drawbacks (e.g., complex design and/or operation, higher manufacturing costs, increased trauma), relative to the other embodiments. Thus, selection of a particular harvesting cannula distal end design will depend on the particular performance criteria sought to be achieved.

"Biological units" include discrete units used in cosmetic, diagnostic, and dermatological procedures, for example, various tissues, including that extracted for biopsies or grafting, fat units, skin units, etc. Examples of the biological units particularly useful with the present invention are hair grafts, or follicles, or "follicular unit(s)." Other biological units may be tissue used for diagnosis of cancer, such as from the areas of the breast, liver, prostate, colon and small bowel, or lungs. Other tissue examples where biopsies are performed include bone, heart and brain tissue. Furthermore, "biological unit" may alternatively be referred to as "biopsy sample," "biopsy specimen," "biological tissue sample," or "biological tissue specimen."

As mentioned above, the term biological units encompasses a number of things, though the present invention is particularly useful in hair harvesting, to provide devices and methods for harvesting follicular units (FUs). As such, the term follicular units (or FUs) will be used herein simply as an example for purposes of describing some embodiments of the present invention with the understanding that it represents more broadly biological units.

The removal tool of the present invention is designed to help retain a biological unit within the tool without damaging it. That is, the removal tool penetrates a body surface, causes a biological unit to enter a lumen therein, and then removes it. It is important that the biological unit goes with or is retained within the removal tool as it is retracted from the body surface. Often, however, the biological unit remains connected in some manner to the tissue that had been surrounding it. For example, a follicular unit may remain attached to the body surface by surrounding connective tissue, even if a vacuum is used in the tool lumen. The surrounding connective tissue tends to pull back the follicular unit from the removal tool which sometimes results either in tearing the follicular unit apart, or simply not retaining it in the removal tool. Likewise, biological specimens that are taken for cancer biopsies, etc. share similar issues with follicular units. That is, it may be important to keep a biopsy specimen intact and not damaged or separated because it may be desirable to see all of the layers of the specimen in exact original order and form to determine an exact location of the cancerous portion (or other problem). The present invention thus provides a retention solution that helps pull biological units free from the surrounding tissue.

Moreover, the present invention provides an improved biological unit removal tool that solves certain problems associated with some prior art designs that have one or two sharp proximally-oriented barbs to retain tissue specimens with a tool. Such barbs tend to either destroy or damage the specimen, and may in any event have insufficient retention structure to hold the biological unit within the tool upon removal. In contrast, the present invention provides a retention structure that is effective in retaining the biological unit within the lumen of the tool without damaging the biological unit.

Various features for improving retention, reducing a flap and transection rates may be incorporated in a single elongated body that is used to penetrate tissue and remove the biological unit. Such features enable a removal tool to be sharp to cut through the epidermis and dermis, and at the same time dull to pass through fatty tissue that surrounds a biological unit such as a follicular unit. Another approach in solving the problems associated with certain prior alt devices is to separate the functions of the removal tool into two different tubes that are utilized in concert, for example a dual-needle or concentric tube can be utilized. It should be understood that various features described herein may be combined with the tool in a similar manner, unless there is some mutually exclusivity between the tools.

FIGS. 3A-3F illustrate the first example of one embodiment of the invention, demonstrating a sequence wherein the removal tool 200 removes a follicular unit FU from below a body surface, denoted by a skin plane 210, of a donor area. The configuration used to illustrate the sequence shown in FIGS. 3A-3F is representative of one configuration that can be used, but not limited to that shown. As seen in the operating sequence of FIGS. 3A-3F, a concentric tube biological unit removal tool 200 comprises an outer elongated body 202 concentrically disposed to slide over an inner elongated body 204. The two elongated bodies 202, 204 are desirably tubular both having cylindrical inner lumens so that they may freely rotate with respect to each other. Alternatively, the cross-section may be other than tubular which might preclude relative rotation. For purpose of brevity, the terms elongated bodies and tubes will hereafter be used interchangeably.

The inner elongated body 204 includes a distal cutting tip 206. Distal tips 206 of varying configurations can be utilized. Certain distal tip designs help to minimize damage to the harvested biological unit and to improve the quality of the harvested specimen. Examples of possible designs can be found in U.S. Patent Publication Number US2008/0234698. For example the distal tip 206 may define a non-circular periphery, be defined by a series of alternating cutting and relief segments which repeat a pattern of constant or varying spacing, or resemble a "crown" shape. In addition, some or all of the relief segments may be offset axially or proximally from the cutting segments. Likewise, the shapes of the cutting segments and relief segments may take a variety of forms. The provision of alternating relatively sharp or cutting segments with relatively dull or relief segments reduce the chance of transection of hair shafts during follicular unit removal. The relative sizes and shapes of the cutting segments and relief segments determine the character and magnitude of cutting versus bluntly dissecting. For example, in some instances a tool that has less cutting ability may be required, such as when harvesting follicular units from a subject that has relatively thin hair follicles which transect more easily, and vice versa.

The cutting tip 206 may have both cutting (e.g., sharp) and dissecting (e.g., blunt) segments around a periphery thereof. As explained above, this arrangement helps prevent transection of biological units, especially follicular units, as the inner tube 204 descends through tissue. The outer elongated body 202 also includes a distal tip 208, though it is preferably blunt so as to be capable of dissection of tissue but relatively incapable of cutting through follicular units or the like.

FIG. 3A shows the tool 200 positioned over a skin plane 210 with the follicular unit FU embedded below the skin plane. The inner tube 204 is seen advanced a predetermined distance beyond the distal tip 208 of the outer tube 202.

FIG. 3B illustrates the tool 200 after having been displaced such that a majority of the exposed portion of the inner tube 204 has penetrated the skin plane 210 such that the distal tip 206 extends past the follicular unit FU. Desirably, suction within an inner lumen of the inner tube 204 helps begin removal of the follicular unit FU.

FIG. 3C illustrates the next step in which the outer tube 202 advances axially over the inner tube 204. Desirably, in this example, the distal tip 208 of the outer tube 202 extends as far as the distal tip 206 of the inner tube 204, or at least extends past the follicular unit. A stop mechanism between the two tubes 202, 204 may be provided to facilitate the co-extension therebetween.

FIG. 3D illustrates proximal retraction of the inner tube 204 within the outer tube 202. The outer tube 202 features a biological unit retention mechanism or member 220 that is actuated upon retraction of the inner tube 204. For purpose of clarity, it should be noted that the terms retention mechanism or retention member will hereafter be used interchangeably. In the exemplary embodiment, the retention member 220, as described in more detail below with respect to FIGS. 4A-4C, includes a plurality of radially movable members 222 that are biased inwardly. Prior to retraction of the inner tube 204, the movable members 222 remain in outer retracted position, and upon removal of the inner tube the movable members constrict inward around the follicular unit FU, as seen in FIG. 3D. In this position, the retention member 220 is said to be in its retention position. In the illustrated embodiment, the movable members 222 are spaced circumferentially around the wall of the outer tube 202 and constrict inward to define an hourglass shape which includes a reduced diameter neck 224 close to the distal tip 208. In the example of FIG. 3D, the reduced diameter neck 224 is located distal to the follicular unit FU so as to retain or capture it within the lumen of the outer tube 202, In other embodiments, the reduced diameter neck 224 may be located somewhere along the length of the follicular unit FU as long as it non-traumatically envelops or "hugs" the follicular unit providing the desired retention without damaging the FU. In the next step shown in FIG. 3E, the entire tool 200 is withdrawn from the skin plane 210. The follicular unit FU is seen captured within the outer tube 202, which remains advanced with respect to the inner tube 204. The positive retention of the follicular unit FU in this manner will effectively extract the follicular unit from any surrounding tissue under the skin plane 210.

FIG. 3F illustrates a subsequent step in which the outer tube 202 has been retracted in the proximal direction with respect to the inner tube 204. Alternatively, of course, the inner tube 204 could be advanced distally with respect to the outer tube 202. This relative movement causes the movable members 222 outward to their retracted position. The inner tube 204 receives the follicular unit FU within its lumen as it advances through the outer tube 202. Viewed another way, the tool 200 captures the follicular unit first within the inner tube 204, transfers it into the outer tube 202, and then transfers it back to the inner tube 204.

FIGS. 4A-4C illustrates an exemplary alternative outer tube 202 of the present invention shown in a relaxed or retentive configuration in which the aforementioned movable members 222 are displaced radially inward. The outer tube 204 includes a proximal end 230 and the aforementioned distal tip 208. A proximal, preferably solid, tubular portion 232 extends approximately half the length of the tube 204. The distal tip 208 comprises a generally tubular ring section 234 preferably having the same diameter as the proximal tubular portion 232. In between the proximal tubular portion 232 and the distal ring section 234, the movable members 222 extend and define the cross-sectional shape of the outer tube 202.

Each of the movable members 222 may be formed from the wall of the outer tube 202, preferably by laser cutting of a tubular blank. In a preferred embodiment, the outer tube 202 may be made of the highly elastic material such as Nitinol, although certain elastic polymers may also be suitable. The movable members 222 are elongated in an axial direction and separated from each other by elongated slots 240, as seen in FIG. 4C. Preferably, each of the slots 240 is relatively narrow, extending axially and terminating at both ends in a pair of enlarged windows 242. The enlarged windows 242 may be circular, as illustrated, such that the slots 240 resemble barbells. FIGS. 4A-4C illustrate a configuration in which there are three evenly spaced slots 240, of identical length, width and shape, with identical windows 242. It will be appreciated that the movable members may be formed with differing numbers of slots 240, unevenly spaced, and of varying lengths, width and shape combinations.

The highly elastic nature of the outer tube 202, such as made with Nitinol, permits the movable members 222 to repeatedly flex inward and outward without fatigue. Nitinol is a material that can be designed so that above certain stresses it becomes super-elastic. The relaxed or retentive configuration with the retention member 220 constricted as in FIG. 3D may be the pre-biased or unstressed shape (which is achieved through a heat-setting or thermal process, as known in the art), and the stressed shape is when the presence of the inner tube 202 expands the retention member 220, thus stressing it above a certain limit so it becomes superelastic (however, the strain levels may not require that the material needs to enter superelastic range). Then, when the inner tube 202 is removed, the retention member 220 again constricts inward and resumes its relaxed shape with no plastic deformation. Such material property is sometimes known as superelasticity, or stress-induced martensitic transformation.

As seen in FIG. 4A, each movable member 222 consists of a proximal trapezoidal segment 244, a central rectangular segment 246, and a distal generally trapezoidal segment 248. In between the segments, and at both ends of each movable member 222 are bend lines, such as the one labeled at 250 at the proximal end of the visible movable member 222. The proximal and distal most bend lines 250 preferably lie in planes that bisect the enlarged windows 242 so that the material cross-section of those points is reduced. The intermediate bend lines 250 are located in the area of the reduced diameter neck 224. The configuration of the outer tube 204 and having movable members 222 is such that the bend lines 250 are located at points where the area moment of inertia of the wall of the tube is low relative to surrounding sections, thus facilitating inward and outward movement of the members 222 by flexion about bend lines.

The distal end further includes short slots 260 that extend from the distal tip 208 of the outer tube 204 to enlarged windows 262 in the middle of the distal segments 248 of each movable member 222. These distal slots 260 further facilitate flexion of the movable members 222. The distal end of the outer tube 204 describes nearly a continuous circular periphery, except for the distal slots 260.

It is important to point out that the particular design of the outer tube 204 comprising the movable numbers 222 is exemplary only, and a number of different configurations are contemplated. For example, in the illustrated embodiment there are three movable members 222 evenly circumferentially distributed around the circumference of the outer tube 204. However, the biological unit retention function of the movable members 222 could conceivably be accomplished by using only one movable member, or more than three. In a preferred embodiment there are movable members disposed substantially around the circumference of the outer tube 204, meaning at least three of them. Likewise, although the movable members 222 are configured to have proximal and distal ends that are solidly connected to the nominal tubular wall of the outer tube 204, with the middle portions flexing inward, alternative embodiments could have just the proximal ends connected to the outer tube, while the distal ends cantilever inward. Indeed, the outer tube 204 may be made of a highly elastic material that stretches and not have any slots at all, such as a solid tube with the neck 224. Those of skill in the art will understand that there are numerous alternative configurations that share the functional attributes of the exemplary embodiment. Alternative movable member 222 configurations can be selected to better suit the type of biological unit being removed, the nature of the surrounding tissue, or the nature of the removal process. Rather than a tube-like movable member, member configurations that are tongue- or petal-like, multi-pronged, prongs equi-distributed, or prongs of varied distributions may be utilized, the prongs being of various lengths, shapes, thicknesses and surface finishes.

Figures 5A, 5B:
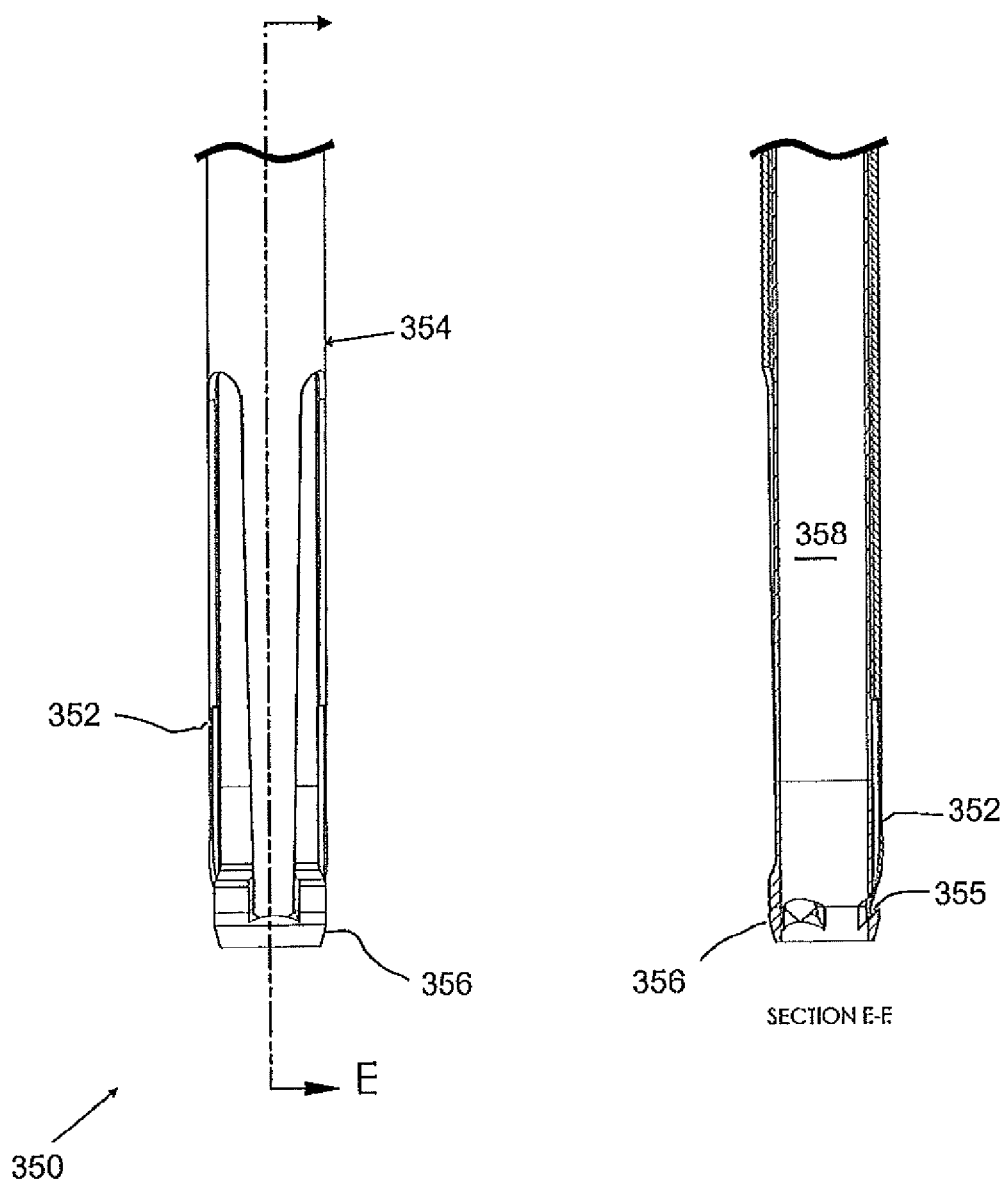
FIGS. 5A and 5B are side and longitudinal sectional views, respectively, of another exemplary embodiment of the biological unit removal tool of the application having a movable retention member in the form of outer tines in a retracted or an undeployed state.
Figures 6A, 6B:
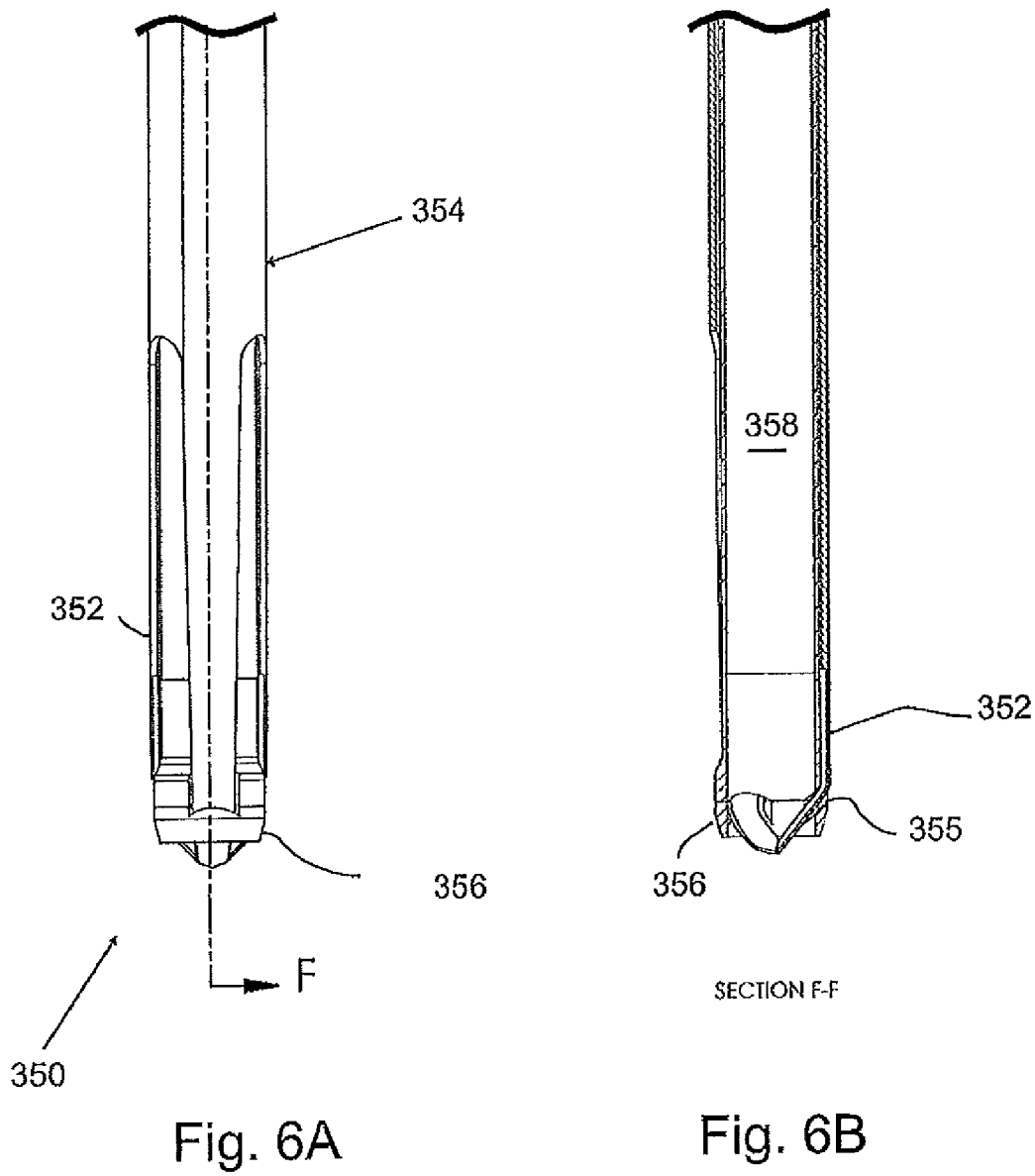
FIGS. 6A and 6B are side and longitudinal sectional views, respectively, of the biological unit removal tool of FIGS. 5A and 5B in a retentive or deployed state.
Figure 8A:
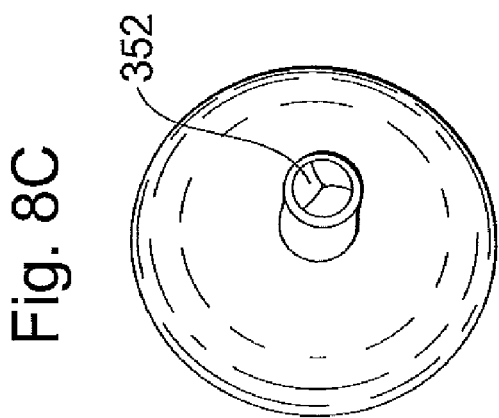
FIGS. 8A-8C are several end views of the biological unit removal tool with the movable retention member of the invention, e.g. tines, showing a progression between the retracted and retentive states.
Figure 8B:
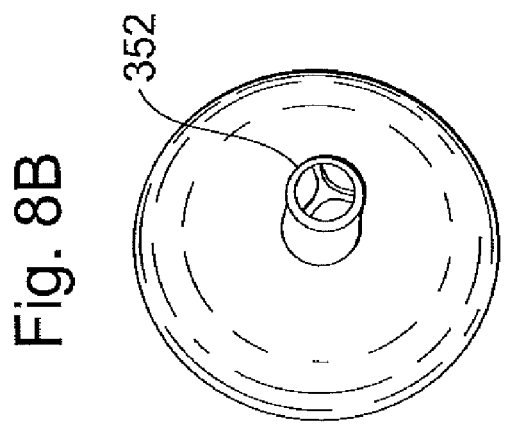
Figure 8C:
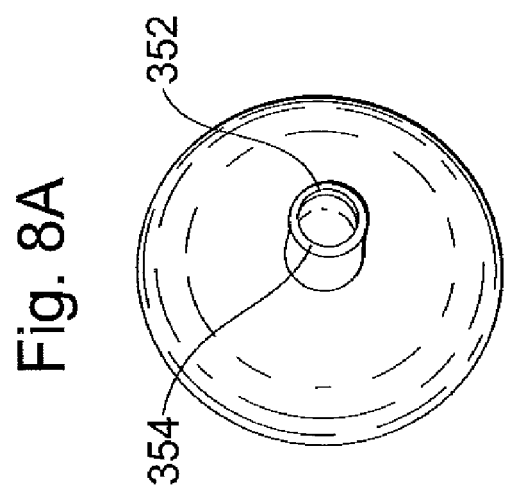

FIGS. 5A and 5B are side and longitudinal sectional views, respectively, of a second exemplary embodiment of a biological unit removal tool 350 according to the invention having a movable retention member in the form of outer tines or blades 352 in an undeployed or retracted state, and FIGS. 6A and 6B show the removal tool in a deployed or retentive state. FIGS. 7A-7E show further views of the biological unit removal tool similar to those of FIGS. 5A and 5B. FIGS. 8A-8C are several end views showing a progression between the retracted and retention positions.

The outer tines or blades 352 are deformable and extend from an outer tube 354. The function of the blades 352 is similar to the embodiment shown in FIGS. 3-4 but with the blades at least partially located on the outer tube 354 and guided through slots, channels or openings 355 located at the distal end 356 of an inner tube 358. One or more slots, channels or openings 355 may be located anywhere proximally to the distal tip. In some embodiments, they may be in close proximity to the distal tip, in other embodiments they may be positioned further from the distal tip along the length of the inner tube. As the outer tube 354 advances distally, the blades 352 are guided and deflected inwardly through the plurality of openings 355 such that the tip portions 360 of the blades 352 coapt or converge, or meet substantially along the longitudinal axis of the lumen of the inner tube 358. This is illustrated in FIG. 7D, which is a view looking into the distal end 356 of the inner tube 358. It can be seen that at least a portion of the retention member (in this case the distal ends of the tines 352) extend beyond the distal tip of the inner tube 358 and converge. It should be noted that, irrigation, for example in the form of a saline fluid, can be injected between the outer tube 354 and the inner tube 358 so as facilitate the capture of the follicular unit, as well as, to minimize the accumulation of blood, tissue, and debris in between the tube members during prolonged procedures by constantly flushing the region between the tube members.

FIGS. 8A-8C are several end views of the biological unit removal tool with the blades or tines 352, showing a progression between the retracted (FIG. 8A) and retentive states (FIG. 8C). In FIG. 8A, it can be seen that substantially no portion of the tines 352 projects across the lumen. In FIG. 8B, the tines 352 are in the process of leaving their retracted position, and project partially across the lumen. Finally, in FIG. 8C, the tines project both into and across the lumen.

Placing the tines or blades on the outside tube 354 and passing them inward through the slot 355 ensures that the lumen is clear when the tines are retracted. In this retracted position substantially no portion of the retention member projects into or across the lumen, as illustrated in FIG. 7C, which once again is a view looking into the distal end 356 of the inner tube 358. The tips of the tines may be located at the opening of the slot for easy re-entry. The position of the tines relative to the slot and the shape of the tines (and/or slot) can be configured, such that even during insertion into tissue or with inward deflection of the tines, the tips of the tines remain substantially removed from the inner lumen, so as not to project into the lumen. The diameter of the inner tube 358 behind the tip portion 356 may have a reduced diameter (which may be incorporated into any of the embodiments) to ensure a low profile. The tines also desirably lie in tracts that are parallel to the long axis and further reduce the profile so that the tines do not extend much beyond the outer diameter of the tip. Three exemplary tines are shown in FIGS. 5A- and 5B, but there could be other numbers of tines employed in various embodiments, for example, two, four, five or more. In addition, the tines 352 may be configured as wires, filaments, fingers, or paddle-shaped, for example. Any potential trauma that may be experienced by the biological unit and/or the surrounding tissue can be reduced by providing tines or blades 352 that are made of Nitinol, titanium, Elgiloy, cobalt chromium, Teflon, silicon, rubber, polymer, plastic or any other materials that are non-traumatic and/or reduce the possibility of damage to the biological unit and/or the surrounding tissue. For example, providing blades 352 having at least tip portions 360 that are made of a material different to the remainder of the material of the blade 352 can achieve this purpose. Alternatively, modifying the surface resistance or roughness of the tip portions 360 mechanically, chemically or environmentally such that the relative motion of the biological unit with respect to the tip portion reduces the potential damage experienced by the biological unit as it is removed. Additionally, removal or reduction of any sharp edges or corners at, near or around the slot, or any other portion of the device, can also be utilized to minimize damage to the biological unit.

FIG. 7E show another aspect of the invention, in which the tip portions 360 of the blades 352 are adapted such that when they coapt or converge, they do not meet substantially along the longitudinal axis of the lumen of the inner tube 358 (in other words, they do not completely close), but stop short of doing that. Therefore, a small gap 362 is created, thus providing another means by which the biological unit and/or the surrounding tissue can be less traumatized during the removal process, especially in those embodiments where the blades or tines 352 converge somewhere along the length of the follicular unit to hold it tight. Trauma experienced by the biological unit and/or the surrounding tissue can be further reduced by adapting the tip portion 360 to minimize such trauma. Such adaptations including, for example, modification to the shape or finish to the tip portion 360 of the blade 352. Adaptations include but are not limited to tip portions that comprise any one or more of non-knife-like, blunt or rounded edges, jagged edges, tapers or other such gradual transitions, crown-like shaping, and roughened finishes. These non-traumatic and non-completely converging tip portions may be incorporated into any of the embodiments of the retention members described herein in reference to various Figures.

In another aspect of the invention (not illustrated), the blade tips 360 may extend to form an elongated section, taking the form of flattened blades for example. In the retention position, the elongated sections of the blade tips 360 extend in a direction that is longitudinal to the lumen formed in the inner tube 358, and coapt such that they physically retain the biological unit along a length of the elongated sections.

FIGS. 9A-9B are side and longitudinal sectional views, respectively, of yet another embodiment of the biological unit removal tool 370 of the present application having a movable tube with blades or tines (not shown) and a protective outer sheath 374. The separate outer sheath 374 fits over an inner tube member 375 which has window features 376 cut, typically by laser, EDM, or conventional machining. The outer sheath 374 has internal longitudinal channels 378 which accommodate the tines and help guide the tines within the windows 376. (Black lines 380 indicate the path for the tines).

One advantage of this embodiment of the invention is that it protects the tines and minimizes possible deflection or disengagement with the windows 376 because of an interaction with the tissue. The windows of the inner tube 375 may also have tabular features within the tube to help guide the tine tip (not shown), especially if the outer sheath is made from polymer, as repeated cycling may damage the polymer portion that interacts with the tine tip. The sheath length can cover the area just at the tip of the inner tube 375, or it could be longer and extend along any portion and up to the full length of the inner tube. A polymer material, for example a heat-shrinkable polymer polyester, can be placed on the outside of the tines of FIG. 5 and FIG. 6, and intimately fitted to the tip portion 356, either by a mechanical means, by an adhesive, or by reshaping the polymer material, or the like, in order to create a outer sheath similar to that depicted in FIG. 9. Furthermore, a section of the tip portion 356 may be formed from a polymer material, either through an overmolding process, by reflowing a covering material through a thermal process, or by creating the shape through the application, shaping, and/or forming of a material, which can be polymer, metal or a combination of the two.

Figure 10A:
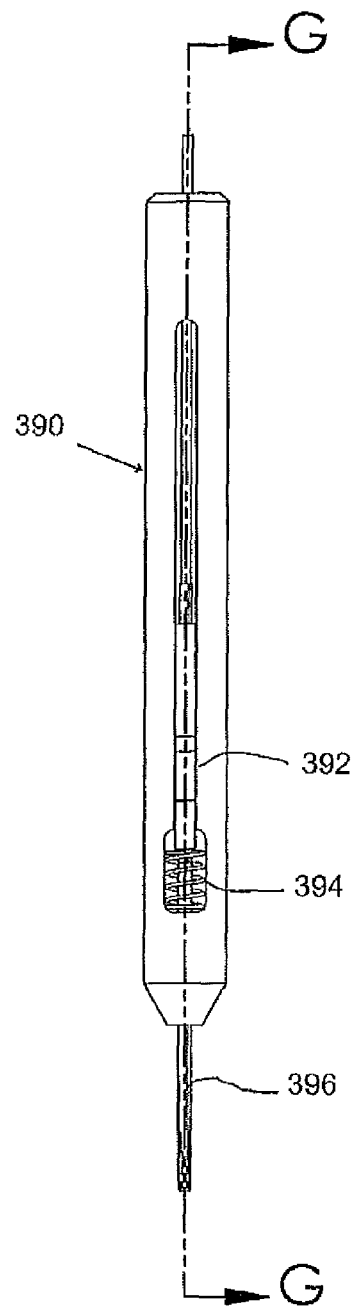
FIGS. 10A-10B are side and longitudinal sectional views, respectively, of an exemplary manually-operated device for controlling the various biological unit removal tools of the invention.
Figure 10B:
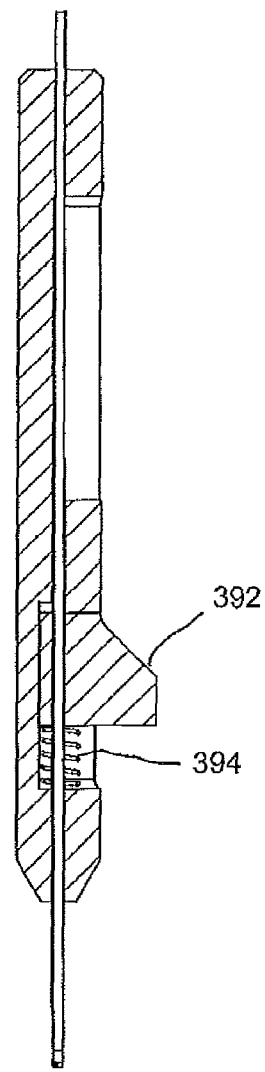

FIGS. 10A-10B are side and longitudinal sectional views, respectively, of an exemplary manual handpiece 390 for controlling the various biological unit removal tools of the present application. The handpiece can be used to actuate/mechanize the tined tip devices previously described. There is a slider 392 that can be finger (thumb) actuated to advance the outer tube 396 distally and cause the tips of the tines to coapt or converge. A return spring 394 causes the slider 392 to return to its original position and "part" the outer tines in the slots or windows and out of the lumen. The "handle" portion can be made from a variety of materials, including but not limited to polymer, aluminum, etc.

FIGS. 11A-11C are exploded and assembled perspective views of a semi-automated handpiece 400 for controlling the various biological unit removal tools of the present application. FIG. 11A is an expanded view of a mechanized tool 400 using an electric motor with a gear reduction head to provide, for example, a 400 rpm rotary speed to provide rotary control of the coring tube (whichever of the inner or outer tubes ends up containing the biological or follicular unit). Two gears offset the drive mechanism so that a cartridge 402 can enter and exit the hollow tapered spindle. The cartridge 402 in this example may be similar to the handpiece 390 described above, or may be another of the concentric tubular assemblies described herein. Essentially, the handpiece 400 provides mechanical power and suction to the cartridge for semi-automated operation thereof. FIG. 11B is a collapsed view showing the cartridge 402 engaged into a hollow spindle 404, and FIG. 11C is a view showing the handle 400 outer body surface.

The cartridge can be inserted into the hollow tapered spindle of the tool and locked in place either with a threaded portion or with a twist-and-lock feature (not shown). The inner tubular member passes all the way through the tool and exits the rear where it may interface to a vacuum collection system. There are two pneumatic actuators shown that act on a collar feature that then pushes on the external tabs of the cartridge. The mechanism may be, for example, a scaled-down version of the manual device of FIGS. 10A-10B FIGS. 12A-12B are side and longitudinal sectional views, respectively, of an exemplary biological unit removal tool or cartridge 410 in accordance with the present application that can be incorporated into a more fully automated system. The cartridge 410 includes a similar actuation mechanism as the manual device, but now the slider has two outwardly extending tabs 412 upon which a pneumatic collar (not shown) may act to provide the linear distal displacement. This assembly may be incorporated into semi- or fully-automated systems, such as described below, and may also be coupled with the mechanized handpiece 400 of FIGS. 11A-11C.

In use, the various biological unit removal tools (or cartridges as termed in some cases above) are operated by a technician or a physician to remove biological units, such as follicular units during a hair harvesting or hair transplantation procedure. In some embodiments, the technician first pierces or penetrates the skin surface with the coring needle or tube, which may be simultaneously rotated. At a predetermined depth, such as between 1-5 mm for follicular units, the technician may halt further rotation of the coring needle. The technician then activates the particular retention member (e.g., tines, blades, wires, petals, etc., as described above) to prevent the biological unit from exiting the lumen of the coring needle. The coring needle may then resume spinning, if able, to help sever the biological unit from its tissue bed. Withdrawal or retraction of the entire removal tool completes the process, with the biological unit remaining in the needle lumen for later expulsion from the distal end, possibly with the aid of compressed air or the like, or proximally through the needle shaft, possibly with the aid of a vacuum source or the like. During certain applications, it is possible to continue rotation or spinning of the coring needle through the whole process.

In an exemplary concentric tube embodiment that represents any of such assemblies described herein, FIGS. 13A-C depict the distal end portion of an alternate embodiment of a tool assembly 520 for harvesting biological units 522 from a body surface 524. The tool assembly 520 includes a pair of coaxially disposed cannulas 526 and 528 that are moveable relative to one another. In particular, a collet 530 holds (and moves) an outer cannula 526 having a blunt distal end opening 532 into the skin surface 524. As the blunt distal end 532 of the outer cannula 526 is moved axially against (thus stretching and tightening, but not penetrating) the skin surface 524, an inner cannula 528 having a sharpened distal end 534 is thrust at high speed through the inner lumen of the outer cannula 526 to pierce the skin surface 524 to a depth of approximately 1 to 2 mm. This allows the outer cannula 528 to continue its progress (i.e., without stopping its relative movement) through the skin surface 524 and into the cutaneous and subcutaneous tissue to a dept of approximately 5-7 mm using blunt dissection (seen in FIG. 13C), to completely capture, for example, the follicular unit 522. Both cannulas 526 and 528 are then withdrawn together from the skin surface 524.

In the concentric tube embodiment of FIGS. 13A and 13B, therefore, the removal tool has two concentric needles or tubes. An inside needle is sharp or semi-sharp, and an outside needle is relatively dull or less able to cut through tissue than the inside needle. The outside needle moves slowly down around the inner needle, whereas the inside needle makes a sudden and rapid punching motion to form a 0.5-2.0 mm deep circular incision. The outside needle can then follow the inside needle into the circular cut made by the inside needle and continue through deeper fatty tissue to a depth of 5-8 mm. The relatively dull edge of the outside needle will guide any hair follicles into both the inner and outer needles instead of transecting them.

An exemplary embodiment implemented with respect to the embodiment of FIGS. 13A-13C may include a rod or piston 540 connected to a proximal end of the outer tube 526 and movable within a plenum chamber 542. Alternating positive and negative pressure within the plenum chamber 542 therefore advances and retracts, respectively, the outer tube 526. The inner tube 528 may be similarly actuated, or may be connected to a mechanical stepper motor or the like (not shown).

FIG. 13A shows the outer tube 526 disposed above the skin surface 524 and positioned over the hair of a follicular unit 522. The inner tube 528 is then advanced rapidly within the outer tube 526 such that the sharp distal end 534 incises a circular cut in the skin surface 524. Subsequently, the outer tube 526 follows over the inner tube 528 and continues deeper below the skin surface 524 to surround the follicular unit 522. At this point, retention means (such as various retention members described above) within the inner or outer tubes may take effect or be actuated, and the assembly pulled free of the skin surface 524 such that the follicular unit 522 is captured therein. Depending on the specific design and application, and depending on the desirable precise order of withdrawal of the inner and outer cannulas from the skin, the retention member may be incorporated into the inner, or outer cannulas, or both. Suction within a lumen 544 of the inner tube 528 may be used to further transfer the follicular unit 522 in a proximal direction.

The concentric tube embodiment described above relies on the formation of a circular incision made by the sharp inner tube after which the less sharp outer tube follows into the tissue. One undesirable possibility is the enlargement or destruction of the clean circular incision by the blunt outer tube. To help prevent such damage, the outer tube may be rotated while the descending into the incision to reduce the chance of catching on the incision from direct linear movement. Alternatively, a small annular space between the inner and outer tubes may be designed so that the outer tube rotates slightly off the axis of the inner tube so as to wobble or be mis-aligned with respect thereto. For that matter, both tubes might be caused to rotate off-center from their own axes and wobble. The wobbling from one or both tubes may allow the outside tube to spiral into the opening created by the inside tube. The removal tool and corresponding process described with reference to FIGS. 13A-C may be substantially automated, and it is especially fitted for use with robotic or computer-controlled systems.

Figure 14A:
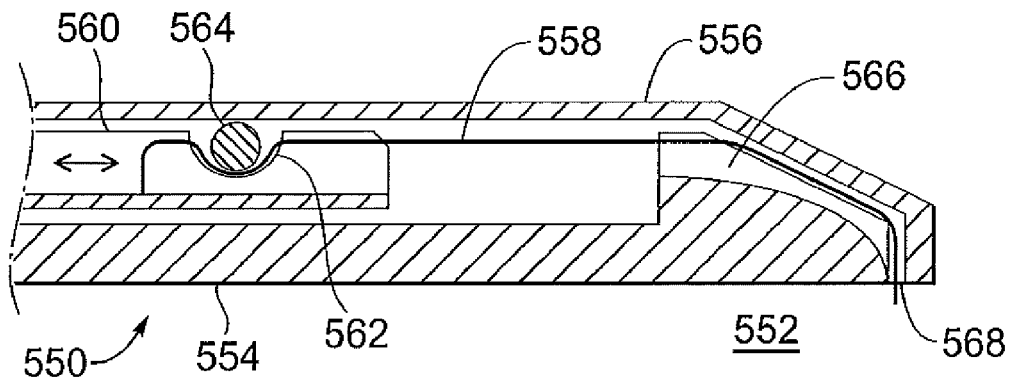
FIGS. 14A and 14B are side and end sectional views, respectively, or a another exemplary embodiment of a biological unit removal tool of the invention having a movable retention member in the form of a plurality of wires shown in a retracted or undeployed state.
Figure 14B:
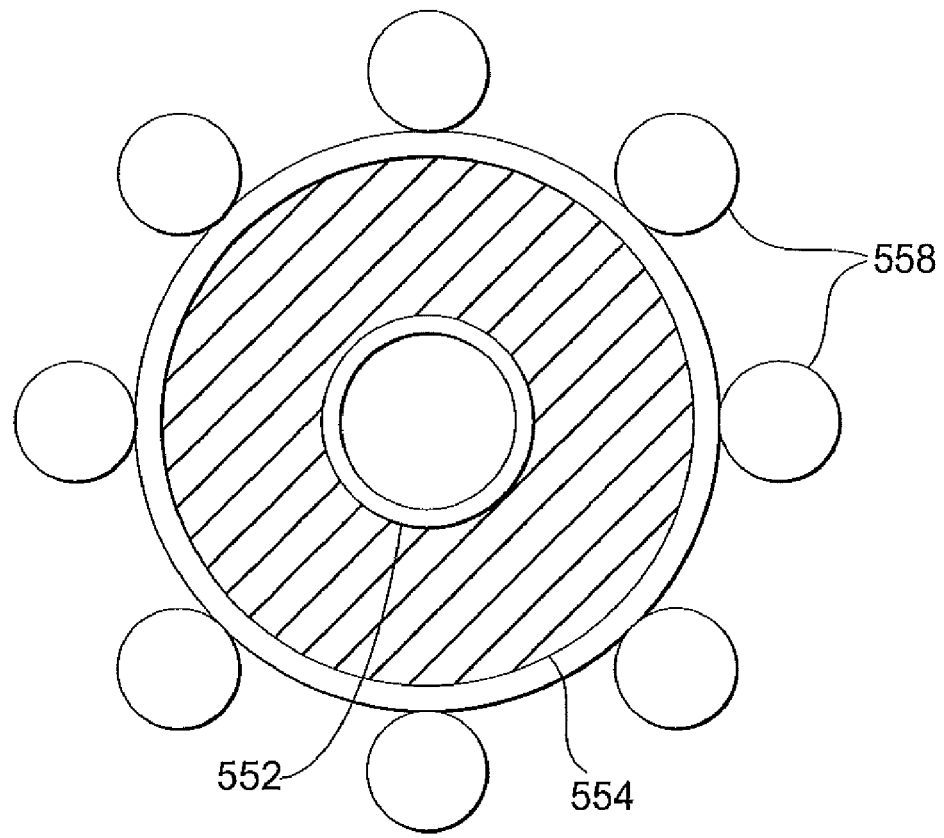

FIGS. 14 A and 14B are side and cross-sectional views, respectively, of another exemplary embodiment of the biological unit removal tool of the invention having a movable retention member in the form of a plurality of movable wires 558. The figures illustrate the biological unit removal tool in its retracted position, in which substantially no portion of the movable member 558 projects into or across the lumen 552. As illustrated in FIG. 14B, this particular configuration employs the use of eight evenly circumferentially-distributed wire fingers, though it will be apparent to the reader that any number of, and a varied distribution of wire fingers may be utilized. The exemplary removal tool 550 has a guide 554 that resides on the outer wall of the member 552 that defines a lumen, and a protective outer sheath 556. The guide 554 has an internal structure 566 such as a channel, or guide which helps guide the movable member 558 in the form of a Nitinol wire finger, for example (though certain other materials that are elastic in nature may also be suitable, such as titanium, Elgiloy, cobalt chromium, Teflon, silicon rubber, polymer or other plastics) through an opening 568 between the guide 554 and the outer sheath 556. The outer sheath 556 may also assist in this guiding process. This configuration protects the Nitinol wire and minimizes possible deflection or disengagement when the Nitinol wire finger interacts with the tissue. The guide 554 and protective outer sheath 556 also house an actuator 560 which moves distal/proximal relative to the lumen and provides a means to control movement of the movable member 558 in and out of the opening 568. In the embodiment shown, actuator 560 is also configured such that it assists the movable member 558 in maintaining its original shape in the radial direction even though it is continually being moved in a longitudinal direction substantially parallel to the longitudinal axis of the lumen 552. Provision of such assistance during both the retention and the retraction process reduces distortion of the wire finger in the radial direction with respect to the lumen 552. In the embodiment shown, the actuator 560 employs the combination of an o-ring 564 and a groove 562 which is shaped to accommodate the o-ring 564 between the groove 562 and the outer sheath 556, the combination keeping the wire in place. The wire finger is additionally solidly affixed to the actuator 560 at the proximal end thereof.

In use, the actuator 560 is moved to advance in the distal direction relative to the lumen, cause the movable member 558 to exit the opening 568, and converge with other movable members 558 in the retention position, in which the movable members 558 assist in retention of a biological unit. In a preferred embodiment, the actuator advances the movable members such that at least a portion of the movable members extends beyond the distal end of the lumen and converges. In another preferred embodiment, the movable member 558 is pre-biased in the retention position, and when retracted back through the opening 568 is in a more stressed state. In yet another preferred embodiment, the movable members are made with a material that permits repeated flexing and outward without fatigue, or exhibits superelastic or stress-induced martenistic transformation properties. In one aspect of the invention, the opening 568 is adapted to guide the movable member in the desired direction, such guiding provided by a ridge) step or other such guiding feature. As with the other embodiments described herein, this removal tool can be actuated manually, or be incorporated into a semi- or fully-automated system.

Figure 15A:
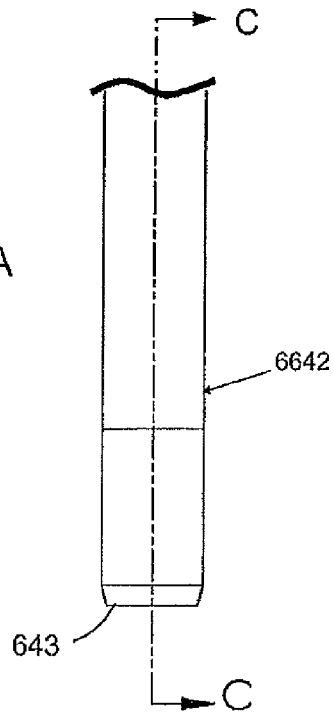
FIGS. 15A and 15B are side and longitudinal sectional views, respectively, of yet another exemplary embodiment of the biological unit removal tool of the invention having a movable retention member in the form of inner tines in a retracted or undeployed state.
Figure 15B:
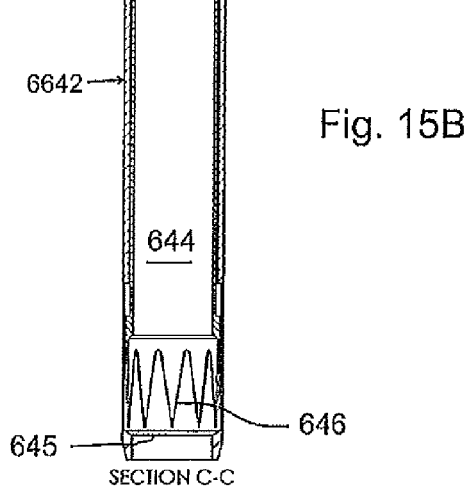
Figure 16A:
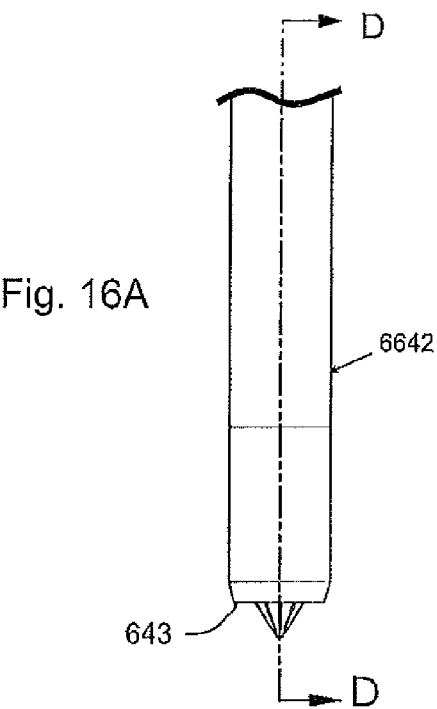
FIGS. 16A and 16B are side and longitudinal sectional views, respectively, of the biological unit removal tool of FIGS. 15A and 15B in a retentive state.
Figure 16B:
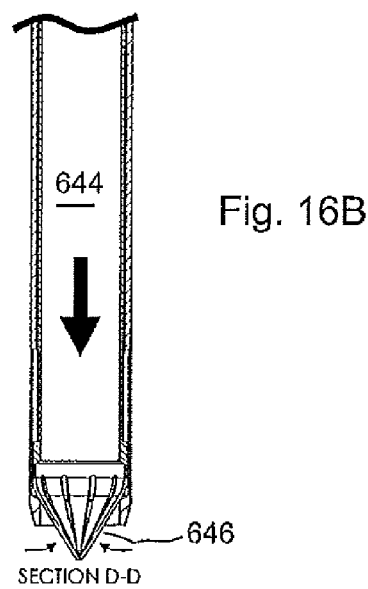

FIGS. 15A and 15B are side and longitudinal sectional views, respectively, of yet another exemplary embodiment of the biological unit removal tool of the invention having a movable retention member in the form of inner tines in a retracted or undeployed state, and FIGS. 16A and 16B show the removal tool in a retention or deployed state. The exemplary removal tool 640 of FIGS. 15-16 has an outer tube or outer member 642 defining a lumen, and an inner tube or inner member 644 with a plurality of movable members or deformable tines 646 mounted on the inner tube. In the retracted position, the deformable tines 646 are flush with the inner diameter of the outer tube 642 and mounted to the distal end of the inner tube 644, which is allowed to move proximal/distal relative to the distal tip 643 of the outer tube. The distal tip 643 has a structure 645 that influences or guides the deformable tines to converge. As illustrated in FIGS. 5 and 6, the structure 645 can take the form of an inner ridge that guides the tines inward as the inner tube is advanced distally such that the tines converge. Alternatively, the structure may take the form of a taper, a step, an incline or any other form that guides the deformable tines to coapt. In the retention position, at least a portion of the retention member, in this embodiment the deformable tines, extend beyond the distal tip of the outer elongated member 642. The inner tube with tines may be made of various materials, including shape memory materials, for example, Nitinol, or Elgiloy, or cobalt chromium, or similar material which accommodates repetitive bending without fatigue (or with more tolerant fatigue properties), if desired, at the base of the tines. As with previous embodiments, the movable retention members need not be in the form of tines, but may be configured as thin wires, filaments, or paddle shaped structures for example, or varying shapes and surface finishes, and of various circumferential distributions.

It is often beneficial to irrigate surgical fields, such as during the removal of biological units, namely multiple follicular units. As the present invention is particularly useful in the context of robotic hair transplantation in which an automated system may be used to harvest multiple follicular units from a body surface, including from the strips of explanted skin containing follicular units. Because of the speed at which such a system works, constant irrigation with, for example, saline will help increase the yield by providing cooling and lubricious fluid at the distal end of the removal tool, it will also help to keep the harvested follicular units moist, as well as aid in the transport of the follicular unit through a vacuum collection system.

While the exemplary embodiment of the present invention may be used in the manual hand-held removal tools, it could also be beneficially incorporated into automated, or semi-automated systems and devices. Specifically, it could be implemented in the robotically-assisted systems and devices, for example, by being connected to the moveable robotic arm. Some exemplary embodiments of such automated systems are described below in reference to FIGS. 17 and 18A-18B.

Figure 17:
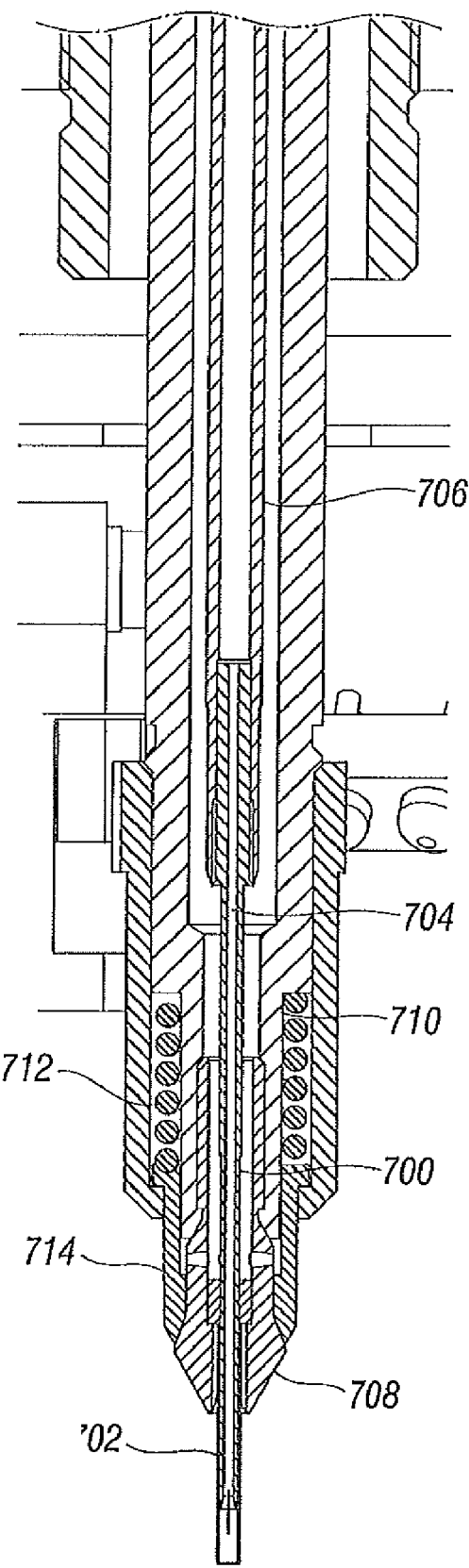
FIG. 17 is an elevational view of one embodiment of a biological unit removal tool incorporated into an exemplary substantially automated system.

FIG. 17 is an elevational view of one embodiment of a concentric tube biological unit removal tool incorporated into an exemplary substantially automated system, such as robotic system. In this exemplary embodiment the removal tool assembly is carried on an automated (e.g., robotic) arm, so that movement of the removal tool relative to the body surface may be performed by movement of the robotic arm relative to the body surface, movement of the removal tool relative to the automated arm, or a combination of each. It should be understood that the assembly of FIG. 17 may be modified to incorporate the exemplary outer elongated body 204 of FIGS. 4A-4C, and caused to operate as seen in FIGS. 3A-3F.

FIG. 17 shows a concentric tube embodiment in which an inner tube 700 slides inside an outer tube 702. A source of reduced pressure communicates with a lumen 704 of the inner needle 700 to create a pressure differential therein for moving biological units through the lumen in a proximal direction. The inner needle may be held at the end of a linearly movable rod 706, while the outer needle is held in a collet 708 and may be rotated or oscillated relative to the inner tube through a spindle 710 on the end of which the collet mounts. A spring 712 acts in a distal direction on a sleeve 714 to maintain the jaws of the collet 708 closed.

In one preferred embodiment, the inner tube 700 has a distal tip that is sharp, or at least that has cutting segments thereon. Desirably, the inner tube 700 translates at a relatively high velocity of between 1-3 m/s, and penetrates the skin (i.e., body surface) to a depth of between 0.25-3.0 mm. After initially penetrating the skin, the inner tube 700 remains under the surface while the outer tube 702 follows. The outer tube 702 is desirably relatively dull compared to the inner tube 700, and enters the skin through the incision that the inner tube 700 created. The outer tube 702 stretches the skin to make the incision somewhat bigger, and enters at a slower velocity, for example, of between 1.0-25.0 mm/s. As mentioned, the outer tube 702 may be rotated or oscillated during its advance. After the outer tube 702 enters the skin, the inner tube 700 may move in concert with the outer tube, remain stationary, or retract as the outer tube continues farther into the skin. Likewise, both tubes 700, 702 may retract from the skin simultaneously, or separately, and may retract at the same or different velocities. As mentioned, suction is desirably applied within the inner tube lumen 704 to aid in biological unit retention. In addition, suction may be applied between the inner and outer tubes 700, 702, and fluids or gas may be supplied between the tubes to aid in retention.

FIGS. 18A and 18B are perspective views of yet another embodiment of the biological unit removal tool 750 incorporated in an exemplary robotically-operated system 752 for hair removal and implantation. Again, the assembly of FIGS. 18A-18B may be modified to incorporate the exemplary outer elongated body 204 of FIGS. 4A-4C, and caused to operate as seen in FIGS. 3A-3F.

A bank of LEDs 754 illuminates a body surface in front of the system so that an imaging device 756, such as a pair of cameras in the illustrated embodiment, obtains a clear picture for transmission back to a monitor (not shown). Various components are mounted for rotation or linear translation of the removal tool 750 at the distal end of the system. Stepper motors, hydraulic cylinders, and the like may be used, and will not be described in great detail herein.

The system may further incorporate a fluid (e.g., saline) delivery subsystem 760 as seen in FIG. 18B near the distal end of the removal tool. FIG. 18B also shows an inner tube 770 having a crown-shaped distal tip 772 and a retention device therein 774. An outer tube 776 surrounds the inner tube 770. Fluid may be delivered in a concentric space between the two tubes 770, 776.

FIG. 18A also illustrates an exemplary subsystem for moving the inner and outer tubes 770, 776 together and with respect to one another. In particular, the inner tube 770 extends along an axis of the subsystem in a proximal direction and is held within a clamp 780 fixed with respect to a movable piston 782. The piston 782 reciprocates within a gas cylinder 784 depending on the pressure within the cylinder, which is controlled by a pneumatic subsystem that will be apparent to one of skill in the art. A distal end of an elongated flexible tube 786 abuts a proximal end of the inner tube 770 within a clamp 780, and defines a continuous extension of the lumen within the inner tube. As mentioned, a suction may be created within the inner tube 770, which continues through the flexible tube 786. The proximal end of the flexible tube 786 engages a storage cartridge (not shown) for receiving and holding follicular units. It should be noted that the inner tube 770 extends a significant length beyond the outer tube 776, and therefore it should be understood that the aforementioned exemplary lengths for the removal tools applies just to the outer tube 776.

The outer tube 776 also reciprocates with a piston 790 within a gas cylinder 792. In particular, a leading end nut 794 holds the outer tube 776 fixed relative to the piston 790. In the illustrated embodiment, as seen in FIG. 18B, the fluid delivery subsystem 760 is located on a distal end of the nut 794. In addition, a gear 796 is keyed to and rotates the piston 790, and thus the outer tube 776. In this particular system, therefore, the inner and outer tubes 760, 776 translate coaxially with respect to one another (or in concert) and are displaced by independently controlled piston/cylinder mechanisms. Of course, the mechanisms for linearly displacing the two tubes 760, 776 may be linear motors or other alternatives. Furthermore, the outer tube 776 rotates with respect to the inner tube 760, and may be rotated in a constant or pulsed manner as it travels in a distal direction over the inner tube 760 and into the skin, as mentioned above.

With an understanding of the aforementioned alternatives for biological unit removal tools, and in conjunction with the exemplary movement subsystem of FIG. 18A, the reader will understand the range of possible uses for the present invention. In a preferred configuration, the subsystem shown in FIG. 18A can, with the help of the visualization tools 754, 756 and a computer monitoring subsystem (not shown), rapidly remove follicular units from a body surface and transfer them to a storage device. One example of a storage device that could be incorporated into an automated system, such as robotic system, for use with the present invention, is shown and described in co-pending Application Ser. No. 60/997,188 filed Sep. 29, 2007 in reference to an exemplary system for robotic hair transplantation.

The structural parameters for the inner and outer tubes 770, 776 are desirably the same as described above for the concentric tubes 700, 702 of FIG. 17. During use, the entire subsystem 752 maneuvers into position (under the control of larger prime movers) so as to locate the distal tip 772 over a particular follicular unit to be removed. In this regard, the visualization subsystem 754, 756 is extremely valuable in pinpointing the location and orientation of the visible hair follicle. The piston/cylinder combination 782, 784 then actuates to punch the inner tube 770 into the skin to a depth of up to 3 mm and at a very high velocity (for example, 1-3 m/s). Preferably, as mentioned, the distal tip 772 includes both sharp and dull segments so that transection of the hair follicles is minimized. Subsequently, the piston/cylinder combination 790, 792 and gear 796 translates with rotation the outer tube 776 over the inner tube 770 in a distal direction. The outer tube 776 desirably has a relatively dull distal tip which enters the circular incision that the inner tube 770 created. The outer tube 776 proceeds at a relatively slow velocity of 1-25 min/s past the end of the inner tube 770 and to a depth of approximately 5-7 mm, surrounding the targeted hair follicle. Suction may be applied to the lumen of the inner tube 770 which continues through the lumen of the outer tube 776 and helps pull free the follicular unit. Also, fluid may be applied by the subsystem 760 to the space between the two tubes to further help remove the follicular unit. Retraction of the outer tube 776, preferably in conjunction with the inner tube 770 and, also in some preferred embodiments with the help of the retention device 774, fully removes the follicular unit from the body surface.

The foregoing illustrated and described embodiments of the invention are susceptible to various modifications and alternative forms, and it should be understood that the invention generally, as well as the specific embodiments described herein, are not limited to the particular forms or methods disclosed, and that many other embodiments are possible within the spirit and the scope of the present invention. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

It will be further appreciated by those skilled in the art that the invention is not limited to the use of a particular system, and that automated (including robotic), semi-automated, and manual systems and apparatus may be used for positioning and actuating the respective removal tools and other devices and components disclosed herein. By way of another example, it will be appreciated by those skilled in the art that while some of the removal tool and apparatus embodiments are described herein in the context of harvesting tissue plugs including hair follicular units, the tools and apparatus are not limited to the harvesting of hair follicular units, and may be equally used for removing various biological units.

While the invention has been described in its preferred embodiments, it is to be understood that the words which have been used are words of description and not of limitation.

Therefore, changes may be made within the appended claims without departing from the true scope of the invention.

What is claimed is:

1. A biological tissue removal tool, comprising:
   an elongated body having a lumen sized to receive a biological unit and a distal end with a distal tip configured to penetrate a body surface; and
   a retention member at least a portion of the retention member axially movable over the elongated body, the retention member radially movable from a retracted position to a retention position, such that in the retention position the retention member protrudes into the lumen of the elongated body and at least a distal tip of the retention member extends beyond the distal tip of the elongated body and converges.

2. The tool of claim 1, wherein the retention member is a tubular member pre-biased in the retention position.

3. The tool of claim 1, wherein the retention member comprises a plurality of one or more of a wire, a filament, a tine, a petal, and a paddle.

4. The tool of claim 3, further comprising a structure configured to guide the plurality of the one or more of a wire, a filament, a tine, and a paddle to converge.

5. The tool of claim 4, wherein the structure comprises any one or more of an opening proximal to the distal tip of the elongate body, a taper at the distal end of the elongated body, and a step at the distal end of the elongated body.

6. The tool of claim 4, wherein the retention member and/or the structure is configured to have substantially no sharp edges or corners.

7. The tool of claim 3, wherein the plurality of one or more of a wire, a filament, a tine, a petal, and a paddle comprises a tip portion, the tip portion configured to create a gap when the plurality of one or more of a wire, a filament, a tine, a petal, and a paddle converges.

8. The tool of claim 1, wherein in the retracted position, substantially no portion of the retention member projects into or across the lumen.

9. The tool of claim 1, wherein the retention member comprises a shape memory material.

10. The tool of claim 1, wherein the retention member comprises material selected from the group consisting of Nitinol, Elgiloy, cobalt chromium, Teflon, stainless steel, titanium, silicon, rubber, polymer, and plastic.

11. The tool of claim 1, wherein the retention member comprises a tip portion, the tip portion configured to minimize trauma to the biological unit.

12. The tool of claim 1, wherein the retention member comprises a tip portion, the tip portion comprising a material different from the remainder of the retention member material.

13. The tool of claim 1, wherein the biological unit comprises any one or more of a follicular unit, a skin sample, a tissue sample, or a biopsy unit, and wherein the tool is selected from a group comprising a hair follicle harvesting cannula, a tissue biopsy punch, and a needle.

14. The tool of claim 1, wherein the tool is configured to be operatively connected to a robotic arm.

15. The tool of claim 1 the elongated body further comprising:
   an inner elongated body and
   an outer elongated body axially movable over the inner elongated body, the outer elongated body comprising the retention member.

16. The tool of claim 15, further comprising a source of irrigation operatively connected to the tool to allow an irrigation fluid to be introduced between the inner elongated body and the outer elongated body.

17. The tool of claim 15, wherein in the retracted position, the retention member takes the shape of the inner elongated body.

18. The tool of claim 15, wherein the biological unit is a follicular unit and the tool is a hair follicle harvesting tool.

19. The tool of claim 1, wherein a shape of the retention member and/or location where the retention member protrudes into the lumen of the elongated body is configured to minimize a contact of the retention member with the biological unit until the retention member is in the retention position.

20. The tool of claim 1, wherein at least a portion of the elongated body over which the retention member is axially movable has a reduced diameter such that the overall diameter of the elongated body with the retention member extending over it is maintained substantially the same.

21. The tool of claim 1, wherein the retention member protrudes into a slot or an opening in a wall of the elongated body, the slot or the opening is located in close proximity to the distal tip of the elongated body.

22. A method of removing biological tissue from a donor area comprising:
   positioning a removal tool adjacent a donor area, the removal tool comprising an elongated body having a lumen sized to receive a biological unit, a distal end with a distal tip configured to penetrate tissue, and a retention member, at least a portion of the retention member movable over the elongated body, the retention member radially movable from a retracted position to a retention position;
   advancing the elongated body to penetrate the donor area and surround a biological unit;
   advancing the retention member over the elongated body and into the lumen of the elongated body to the retention position such that at least a distal tip of the retention member extends beyond the distal tip of the elongated body and converges; and
   withdrawing the elongated body and the retention member to remove the biological unit from the donor area with assistance of the retention member.

23. The method of claim 22, wherein the retention member is pre-biased in the retention position, and wherein advancing the retention member allows it to return to its biased position.

24. The method of claim 22, wherein the retention member comprises a plurality of movable members, and advancing the retention member further comprises converging the plurality of the movable members.

25. The method of claim 22, wherein the biological unit is a follicular unit, and wherein the method comprises robotically assisted hair harvesting method.

26. A method of removing a follicular unit from a donor area comprising:
   positioning a removal tool adjacent a donor area, the removal tool comprising an inner elongated body having a lumen sized to receive a follicular unit and a distal tip adapted to cut through tissue, an outer elongated body having a retention member radially movable between a retracted position and a retention position;
   advancing the inner elongated body to penetrate the donor area and surround a follicular unit;
   advancing the outer elongated body with the retention member concentrically over the inner elongated body and into the lumen of the inner elongated body so that the retention member moves from the retracted position to the retention position and a distal tip of the retention member extends past the follicular unit; and withdrawing the inner and outer elongated body to remove the follicular unit from the donor area with assistance of the retention member.

27. The method of claim 26, further comprising introducing a fluid between the inner elongated member and the outer elongated member.

28. The method of claim 26, wherein advancing the outer elongated body with the retention member into the lumen of the inner elongated body comprises advancing through a slot or an opening in a wall of the inner elongated body.

\* \* \* \* \*